US012753428B2

(12) United States Patent
Schiavinato Eberlin et al.

(10) Patent No.: US 12,753,428 B2
(45) Date of Patent: Oct. 6, 2026

(54) IDENTIFYING AND CLASSIFYING MICROORGANISMS

(71) Applicants: BOARD OF REGENTS, THE UNIVERSITY OF TEXAS SYSTEM, Austin, TX (US); THE TRUSTEES OF INDIANA UNIVERSITY, Bloomington, IN (US)

(72) Inventors: Livia Schiavinato Eberlin, Austin, TX (US); Sydney Povilaitis, Austin, TX (US); Marta Sans Escofet, Austin, TX (US); Jialing Zhang, Austin, TX (US); Lindsey M. Kirkpatrick, Carmel, IN (US)

(73) Assignees: BOARD OF REGENTS, THE UNIVERSITY OF TEXAS SYSTEM, Austin, TX (US); THE TRUSTEES OF INDIANA UNIVERSITY, Bloomington, IN (US)

( * ) Notice: Subject to any disclaimer, the term of this patent is extended or adjusted under 35 U.S.C. 154(b) by 643 days.

(21) Appl. No.: 17/921,734

(22) PCT Filed: Apr. 27, 2021

(86) PCT No.: PCT/US2021/029308
§ 371 (c)(1),
(2) Date: Oct. 27, 2022

(87) PCT Pub. No.: WO2021/222182
PCT Pub. Date: Nov. 4, 2021

(65) Prior Publication Data

US 2023/0167478 A1 Jun. 1, 2023

Related U.S. Application Data

(60) Provisional application No. 63/032,394, filed on May 29, 2020, provisional application No. 63/016,129, filed on Apr. 27, 2020.

(51) Int. Cl.

| | |
|---|---|
| ***C12Q 1/02*** | (2006.01) |
| ***G01N 33/68*** | (2006.01) |
| ***H01J 49/04*** | (2006.01) |

(52) U.S. Cl.
CPC ........... *C12Q 1/02* (2013.01); *G01N 33/6848* (2013.01); *H01J 49/0431* (2013.01); *G01N 2333/24* (2013.01); *G01N 2333/31* (2013.01); *G01N 2333/315* (2013.01)

(58) Field of Classification Search
CPC ......... C12Q 1/02; C12Q 1/04; G01N 33/6848
See application file for complete search history.

(56) References Cited

U.S. PATENT DOCUMENTS

| | | | |
|---|---|---|---|
| 5,711,816 | A | 1/1998 | Kirlin et al. |
| 5,742,050 | A | 4/1998 | Amirav et al. |
| 6,803,566 | B2 | 10/2004 | Van Berkel |
| 10,643,832 | B2 | 5/2020 | Eberlin et al. |
| 11,289,320 | B2 | 3/2022 | Pringle et al. |
| 2003/0193020 | A1 | 10/2003 | Van Berkel |
| 2004/0014227 | A1 | 1/2004 | Frederik et al. |
| 2004/0059530 | A1 | 3/2004 | Paulse et al. |
| 2005/0061967 | A1 | 3/2005 | Shvartsburg et al. |
| 2006/0169030 | A1 | 8/2006 | Stewart et al. |
| 2006/0292607 | A1 | 12/2006 | Caprioli |
| 2007/0114375 | A1 | 5/2007 | Pevsner et al. |
| 2007/0135779 | A1 | 6/2007 | Lalomia et al. |
| 2007/0197954 | A1 | 8/2007 | Keenan |
| 2008/0156985 | A1 | 7/2008 | Venter et al. |
| 2008/0261263 | A1 | 10/2008 | Allardyce et al. |
| 2009/0302211 | A1 | 12/2009 | Takats |
| 2010/0148057 | A1 | 6/2010 | Jarrell et al. |
| 2010/0176287 | A1 | 7/2010 | Ribbing et al. |
| 2010/0224013 | A1 | 9/2010 | Van Berkel et al. |
| 2011/0253889 | A1 | 10/2011 | Ishimaru et al. |

(Continued)

FOREIGN PATENT DOCUMENTS

| | | | |
|---|---|---|---|
| WO | 2018045208 | A1 | 3/2018 |
| WO | 2020104621 | A1 | 5/2020 |

OTHER PUBLICATIONS

Kertesz et al. 2005 (Automation of a Surface Sampling Probe/Electrospray Mass Spectrometry System; Anal. Chem. 77:7183-7189). (Year: 2005).*

(Continued)

*Primary Examiner* — Mary Maille Lyons
(74) *Attorney, Agent, or Firm* — Meunier Carlin & Curfman LLC

(57) ABSTRACT

In a general aspect, microorganisms [e.g., bacteria, etc.) are identified and detected. In some examples, a liquid solvent is supplied through a first channel of a sampling probe to an internal reservoir of the sampling probe; a fixed volume of the liquid solvent in the internal reservoir is held in direct contact with a sample surface for a period of time to form a liquid analyte; gas is supplied to the internal reservoir through a second channel of the sampling probe; the liquid analyte is extracted from the internal reservoir through a third channel of the sampling probe; the liquid analyte is transferred to a mass spectrometer; the mass spectrometer processes the liquid analyte to produce mass spectrometry data; and the mass spectrometry data are analyzed to detect and identify a microorganism [e.g., acteria, fungi, or another type of microorganism) present at the sample surface.

13 Claims, 21 Drawing Sheets

(56) References Cited

U.S. PATENT DOCUMENTS

| | | | |
|---|---|---|---|
| 2011/0284735 | A1 | 11/2011 | Van Berkel et al. |
| 2012/0053065 | A1 | 3/2012 | Van Berkel |
| 2012/0080592 | A1 | 4/2012 | Wiseman et al. |
| 2012/0083045 | A1 | 4/2012 | Van Berkel et al. |
| 2012/0149009 | A1 | 6/2012 | Levis et al. |
| 2013/0131470 | A1 | 5/2013 | Galinkin et al. |
| 2014/0216177 | A1 | 8/2014 | Van Berkel et al. |
| 2014/0353488 | A1 | 12/2014 | Takats |
| 2015/0230738 | A1 | 8/2015 | Cooks et al. |
| 2016/0041138 | A1 | 2/2016 | Pycke et al. |
| 2016/0047831 | A1 | 2/2016 | Cooks et al. |
| 2016/0181078 | A1 | 6/2016 | Kovarik |
| 2016/0181079 | A1 | 6/2016 | Berkout |
| 2016/0296215 | A1 | 10/2016 | Bouamrani et al. |
| 2016/0299041 | A1 | 10/2016 | Kertesz et al. |
| 2016/0314956 | A1 | 10/2016 | Cooks et al. |
| 2016/0341712 | A1 | 11/2016 | Agar |
| 2016/0355865 | A1 | 12/2016 | Bierbaum et al. |
| 2017/0014149 | A1 | 1/2017 | Nakayashiki et al. |
| 2018/0038838 | A1 | 2/2018 | Karancsi et al. |
| 2018/0059119 | A1 | 3/2018 | Takats et al. |
| 2018/0059126 | A1 | 3/2018 | Jones et al. |
| 2018/0067097 | A1 | 3/2018 | Eberlin et al. |
| 2018/0100839 | A1 | 4/2018 | Van Berkel |
| 2018/0144916 | A1 | 5/2018 | Richardson et al. |
| 2018/0158661 | A1* | 6/2018 | Eberlin .................. G01N 30/72 |
| 2019/0212338 | A1 | 7/2019 | Koskinen et al. |
| 2020/0305723 | A1 | 10/2020 | Eberlin et al. |
| 2022/0034900 | A1 | 2/2022 | Morozumi et al. |

OTHER PUBLICATIONS

Soufi et al. 2016 (Mass Spectrometry-Based Bacterial Proteomics: Focus on Dermatologic Microbial Pathogens; Frontiers in Microbiology vol. 7, Article 181, pp. 1-7). (Year: 2016).*

International Search Report and Written Opinion received in PCT/US2021/029308 mailed Aug. 5, 2021, 12 pages.

Extended European Search Report mailed Mar. 28, 2024 in corresponding EP Application No. 21795674.7 (11 pages).

Monge Maria Eugenia et al: "Mass Spectrometry: Recent Advances in Direct Open Air Surface Sampling/Ionization", Chemical Reviews, 2013, 113(4),2269-2308.

Zhang, J et al., Nondestructive tissue analysis for ex vivo and in vivo cancer diagnostics using a handheld mass spectrometry system. Science transnational medicine. 2017, 9(406), eean3968.

* cited by examiner

600

620

750

IDENTIFYING AND CLASSIFYING MICROORGANISMS

CROSS-REFERENCE TO RELATED APPLICATIONS

This application claims priority to U.S. Provisional Patent Application No. 63/016,129, filed Apr. 27, 2020, entitled "Identifying and Classifying Microorganisms;" and U.S. Provisional Patent Application No. 63/032,394, filed May 29, 2020, entitled "Identifying and Classifying Microorganisms." Each of the above-referenced priority documents is hereby incorporated by reference in its entirety.

GOVERNMENT SUPPORT CLAUSE

This invention was made with government support under Grant No. R21 HD106614 awarded by the National Institutes of Health. The government has certain rights in the invention.

BACKGROUND

The following description relates to identifying and classifying microorganisms.

Microbial identification is important in many contexts, for example, for detecting environmental contaminants, disease surveillance, and providing adequate health care. For instance, microbial identification can be critical to enforce antimicrobial stewardship programs, which optimize the prescription of antibiotics to promote positive patient outcomes while preventing the spread of antimicrobial resistance (AMR). Patients with acute infections often receive broad spectrum antibiotics, which can be ineffective and promote AMR, and patients with less severe illness may wait up to 72 hours before they can receive targeted antimicrobial therapy.

DETAILED DESCRIPTION

Figure 1:
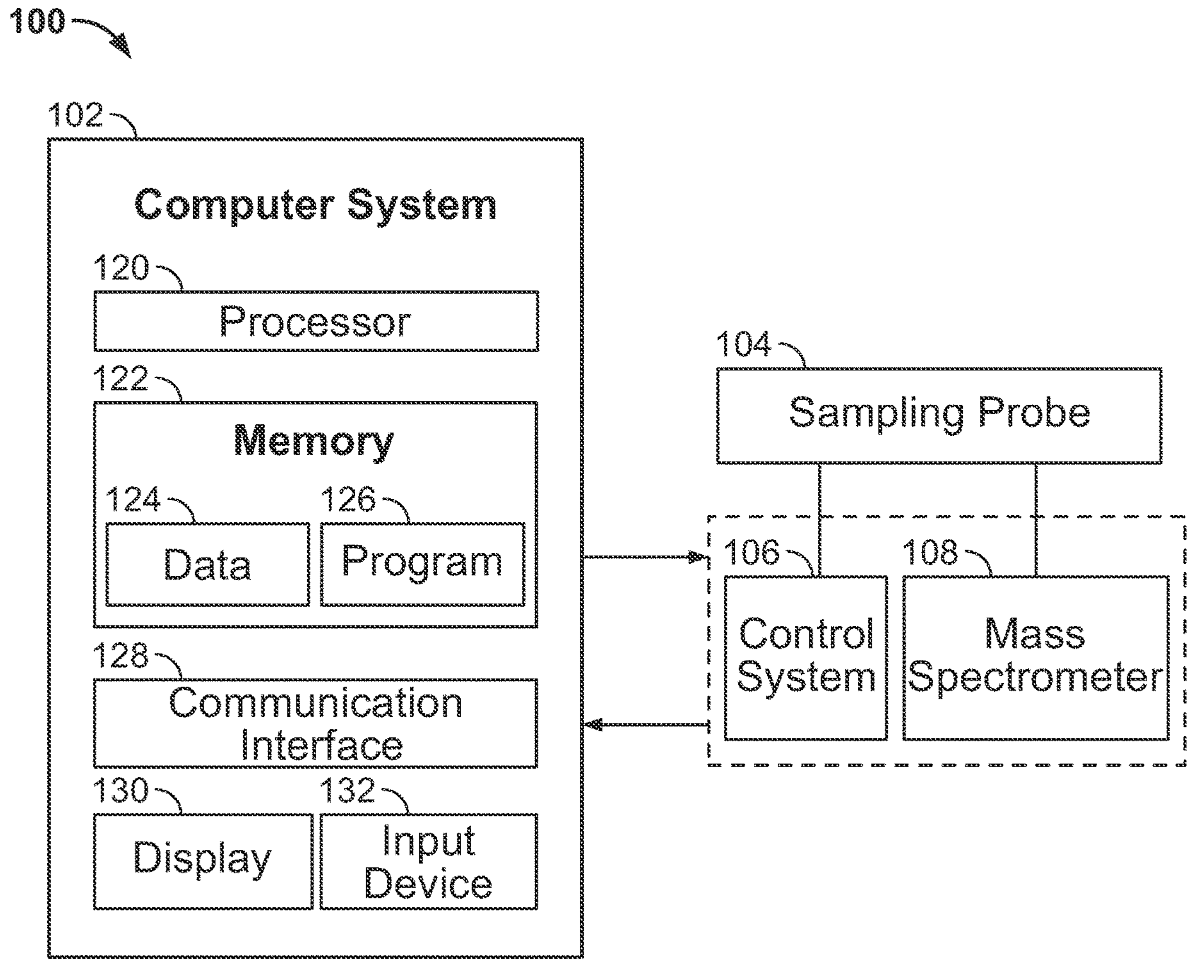
FIG. 1 is a schematic diagram of an example microorganism identification system.

In some aspects of what is described here, a microorganism identification system for identification and classification of microorganisms includes a sampling probe, a control system, and a mass spectrometer. The sampling probe may be positioned on a sample surface (which may contain microorganisms of interest) to receive a liquid solvent from the control system, to form an analyte (which may include at least a portion of a microorganism from the sample surface), and to transfer the analyte to the mass spectrometer. The analyte received from the sampling probe can be processed by the mass spectrometer. In some instances, microorganisms contained on the sample surface can be identified and classified using a statistical model.

In some implementations, the methods and systems disclosed here may provide technical advantages and improvements relative to conventional techniques. In some instances, the methods and systems described here may provide versatile sampling and direct identification of microorganisms. In some instances, the methods and systems described here may accelerate the development of a targeted antibiotic. In some instances, the methods and systems described here may accelerate and allow selection of an appropriate targeted antibiotic for a patient in clinical care. In some implementations, the methods and systems described here may improve patient outcomes and prevent spreading of antimicrobial resistance. Additionally and alternatively, simplified operational steps and system design may be utilized without requiring experienced professionals to perform such analysis. In some cases, the methods and systems described here can reduce biohazardous risks associated with conventional techniques. For example, alternative ambient sampling mass spectrometry (MS) techniques (e.g., desorption electrospray ionization (DESI) MS, paper spray ionization (PSI) MS and rapid evaporative ionization (REI) MS) produce microdroplets or aerosols containing infectious materials in an open environment, which may pose a serious biohazardous risk to the analyst. In some cases, a combination of these and potentially other advantages and improvements may be obtained.

In some implementations, the systems and techniques described here enable molecular based identification of microorganisms on a rapid timescale with minimal sample preparation, which can expedite identification of pathogenic bacteria and provide other advantages over conventional techniques. Rapid and accurate identification of infectious agents is critical to allow selection of specific and targeted treatment options and improve outcomes for patients with bacterial infections. Unspecific therapy regimens with broad spectrum antibiotics can lead to many short- and long-term adverse effects for patients including allergic reactions, antibiotic-related diarrhea, potential bacterial resistance, and *Clostridium difficile* colitis. Targeted, pathogen-specific antibiotics offer better patient outcomes and often help avoid many of the negative consequences of broad-spectrum antibiotic therapy. Identification at Gram type, genus, species and strain level may inform selection of even more targeted antibiotics and prevent overuse of broad-spectrum antibiotics. For example, Gram type identification is sufficient in most cases to prescribe the moderate spectrum lincosamide antibiotics, but species-level identification is most beneficial as many narrow spectrum antibiotics may have activity against only some species, such as aminoglycoside antibiotics which are specifically active against *Staphylococcus aureus* but not *Staphylococcus epidermidis* or *Streptococcus* species. Further, strain level characterization of pathogenic bacteria may offer insight into virulence, antimicrobial resistance, and is especially useful for public health surveillance. In the clinical setting, bacteria are isolated from patient specimens and cultured for at least 24 hours, after which several methods can be used for identification. Traditionally, the gold standards for bacterial identification are culture and serological assays where a series of selective growth conditions and media are used to identify bacteria based on phenotype. These methods require substantial expertise, are time- and labor-intensive, can delay targeted antibiotics by days, and as a result, many infections are routinely treated empirically or with broad-spectrum antibiotics. Molecular-based methods including polymerase chain reaction (PCR), which identifies bacteria based on 16S ribosomal RNA sequences, have reduced the time required for bacterial identification to hours. While PCR offers an exciting alternative for bacterial identification, this method requires user expertise and specific, expensive reagents and therefore is still resource intensive. Thus, systems and methods that provide rapid detection and identification of bacteria and other microorganisms can provide significant advantages over these traditional approaches.

Figure 3:
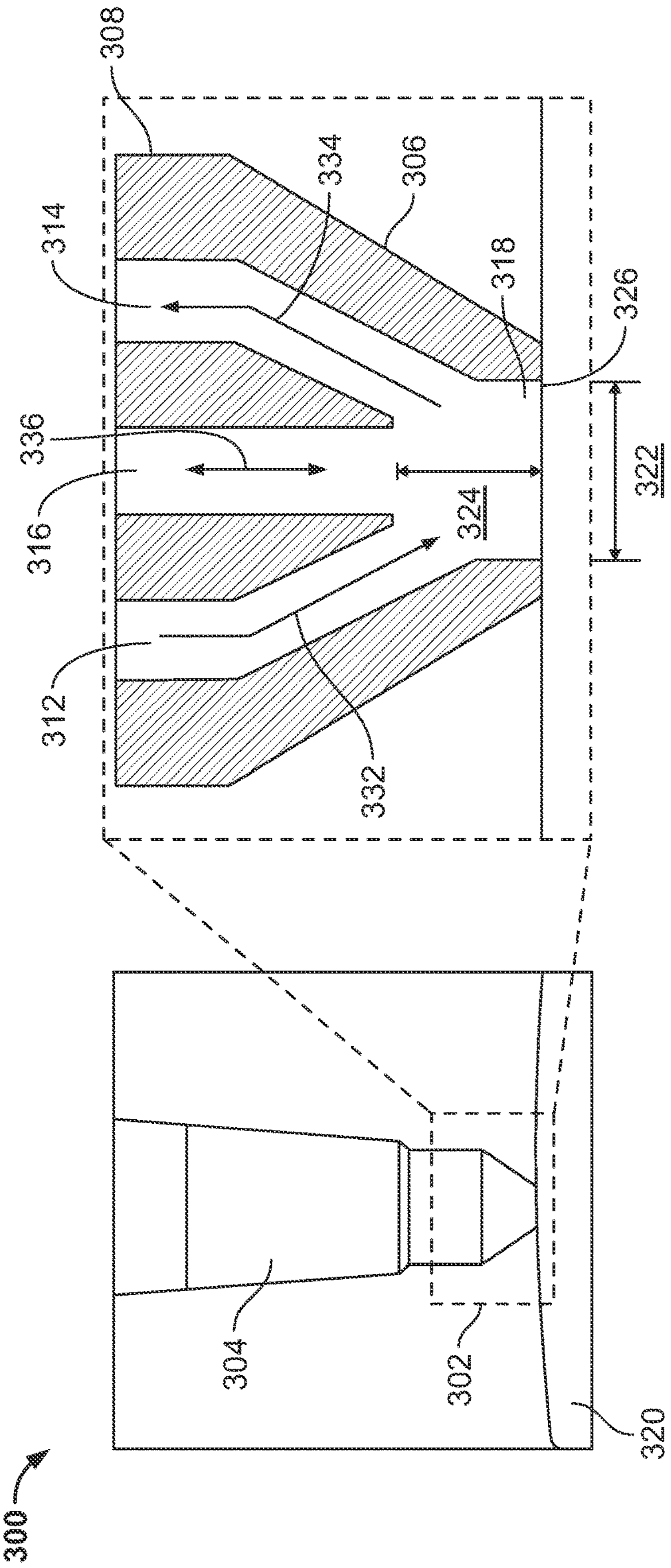
FIG. 3 is a schematic diagram showing aspects of a sampling probe in an example microorganism identification system.

In some implementations, the sampling probe may include a probe tip and a housing. In some implementations, the probe tip, e.g., the probe tip 302 as shown in FIG. 3, may include one mandrel end and one cylindrical end. For example, the mandrel end in a tapered cylindrical shape may be used for contacting a sample surface, which may contain microorganisms such as bacteria. For example, the cylindrical end may be used to engage with a receiving end of the housing. In some implementations, the probe tip may include three internal channels creating three internal pathways and an internal reservoir. In some examples, the probe tip may include a liquid supply channel (e.g., the liquid supply channel 312), a liquid extraction channel (e.g., the liquid extraction channel 314), and a gas channel (e.g., the gas channel 316). In some implementations, the liquid supply and extraction channels may be configured to provide fluidic communication with the control system and the mass spectrometer.

In some implementations, the liquid supply channel is configured for receiving a liquid solvent from an external container, for guiding the liquid solvent to the internal reservoir at the probe tip, where the liquid solvent may be in direct contact with the sample surface through an opening, and for filling up at least a portion of the internal reservoir with the liquid solvent. In some implementations, the liquid extraction channel is configured for obtaining an analyte from the internal reservoir by extracting at least a portion of the liquid solvent carrying suspended microorganisms, and for guiding the analyte to the transfer tube.

In some implementations, a fixed volume of liquid solvent is communicated into the probe tip. The fixed volume of fluid can be retained within the internal reservoir while in direct contact with the sample surface for a controlled amount of time, to form a liquid analyte containing molecules from the sample surface. The liquid analyte may then be extracted (e.g., as a single, discrete droplet of fluid) from the internal reservoir through the liquid extraction channel for analysis. In some instances, the liquid analyte is produced by the sampling probe in a non-destructive manner that does not damage the sample surface. For instance, the probe may extract the liquid analyte from a tissue site or tissue sample without causing any detectable damage or destruction to the tissue.

In some implementations, the microorganism identification system includes a mass spectrometer that produces mass spectral data which can include molecular profiles of microorganisms for bacterial differentiation and identification. In some implementations, the microorganism identification system includes a statistical model to provide separations of groups on the genus and species level according to the molecular profiles. In some instances, a statistical model, e.g., a multi-level LASSO model, together with the microorganism identification system may allow a discrimination of isolates at Gram type, genus, and species levels. In some implementations, the microorganism identification system may be used to identify infectious agents directly from human pus fluid, cerebrospinal fluid, infected bone tissue or other biological specimens.

FIG. 1 is a schematic diagram of an example microorganism identification system 100. As shown in FIG. 1, the example system 100 includes a computer system 102, a sampling probe 104, a control system 106, and a mass spectrometer 108. In some implementations, the example system 100 may be used for qualitatively and quantitatively identification and classification of microorganisms, e.g., bacteria, fungi, viruses, algae, and protozoa. In some examples, the example system 100 may include additional or different components, and the components may be arranged as shown or in another manner.

In some implementations, the system 100 is used to evaluate biological samples (e.g., in vivo or ex vivo tissue samples), medical tools, industrial equipment and facilities, agricultural environments, or any other types of materials or equipment. In some cases, the system 100 is used in a medical environment, for example, during a surgical procedure, to identify and classify microorganisms present at an in vivo tissue site. In some cases, the system 100 is used in a laboratory environment, for example, to evaluate ex vivo tissue samples collected from a subject. The system may also be used in other environments, for example, in food or drug preparation facilities, to identify the presence of microorganisms.

In the example shown in FIG. 1, the computer system 102 includes a processor 120, memory 122, a communication interface 128, a display device 130, and an input device 132. In some implementations, the computer system 102 may include additional components, such as, for example, input/output controllers, communication links, power, etc. In some instances, the computer system 102 may be configured to control operational parameters of and to receive data from the control system 106, and the mass spectrometer 108. The computer system 102 can be used to control the control system 106 to deliver liquid solvents to the sampling probe 104; and to control the extraction of analytes containing extracted biomolecules and suspended microorganisms from the sampling probe 102. In some implementations, the computer system 102 may be used to implement one or more aspects of the systems and processes described with respect to FIGS. 2, and 3, or to perform another type of operations. In some implementations, the computer system 102 includes a separate control unit associated with and providing specific control functions to the control system 106. In some instances, the control unit may be implemented as the control unit 204 or in another manner.

In some implementations, the computer system 102 may include a single computing device, or multiple computers that operate in proximity to the rest of the example system 100 (e.g., the control system 106, and the mass spectrometer 108). In some implementations, the computer system 102 may communication with the rest of the example system 100 via the communication interface 128 through a communication network, e.g., a local area network (LAN), a wide area network (WAN), an inter-network (e.g., the Internet), a network comprising a satellite link, and peer-to-peer networks (e.g., ad hoc peer-to-peer networks).

Figure 2:
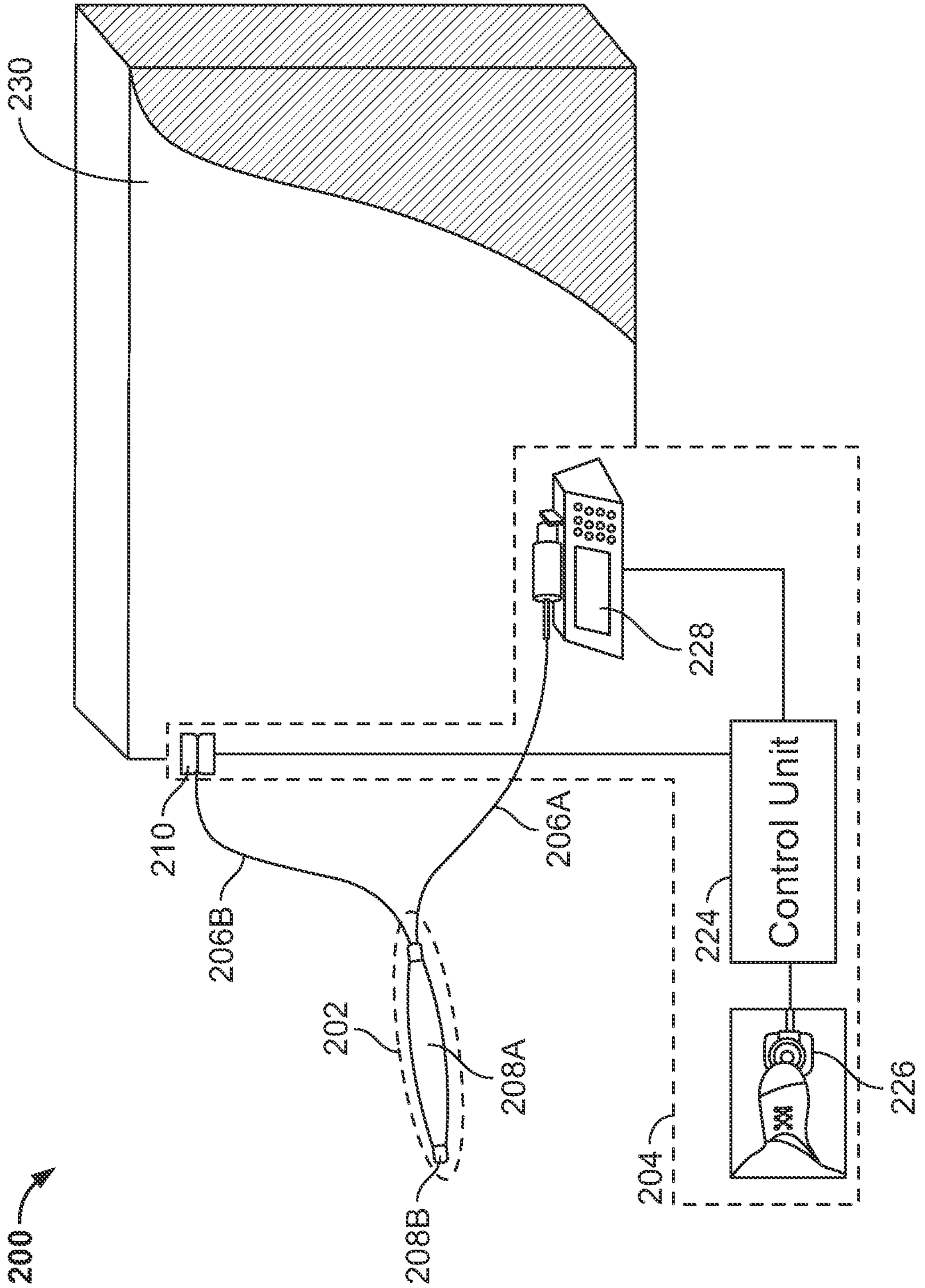
FIG. 2 is a schematic diagram showing aspects of an example microorganism identification system.

In some implementations, the sampling probe 104 may be configured to provide fluidic communication with the control system 106 and the mass spectrometer 108 via transfer tubes. In some instances, the sampling probe 104 may receive liquid solvent from the control system 106, guide the liquid solvent to a sample surface with microorganisms, obtain an analyte by extracting at least a portion of the liquid solvent, and deliver the analyte containing suspended microorganisms to the mass spectrometer 108. In some implementations, the sampling probe 104 may include a probe tip, which may include multiple internal liquid/gas channels and an internal reservoir, e.g., the channels 312, 314, 316 and the internal reservoir 318 as shown in FIG. 3. In some implementations, the sampling probe 104 may be composed of materials, such as synthetic polymers that are biologically compatible and resistant to chemicals used. In some examples, the sampling probe 104 may be implemented as the sampling probes 202, 300 as shown in FIGS. 2-3 or in another manner.

The example control system 106 controls the movement of fluid in the system 100. In some implementations, the control system 106 may include a mechanical pumping system and one or more mechanical valves. In some instances, the mechanical pumping system contains a mechanical pump that is controlled by the computer system 102. For example, the mechanical pumping system may be implemented as the mechanical pumping system 228 as shown in FIG. 2 or in another manner. In some instances, the control system 106 may provide high-precision, microfluidic dispensation of the liquid solvent to the internal reservoir of the sampling probe 104. In some instances, a control unit of the control system 106 (e.g., the control unit 224 in FIG. 2) may be configured to trigger and control a sampling process by controlling the mechanical pumping system and the one or more mechanical valves. In some instances, the control unit of the control system 106 may be configured to simultaneously trigger a data collection process by the mass spectrometer 108. In some implementations, the liquid solvent may include sterile water, ethanol, methanol, acetonitrile, dimethylformamide, acetone, isopropyl alcohol, or a combination. In some implementations, the liquid solvent may contain bacteriolytic enzymes or other compounds for breaking down microbial cell wall and membrane structures or other solvent additives such as acids or bases for ionization enhancement, or antibiotics for susceptibility testing.

In some implementations, an analyte carrying the suspended microorganisms and molecules extracted from the microorganisms may be received by the mass spectrometer 108. In some implementations, the analyte may be extracted from the sampling probe 202 by creating a low pressure in the mass spectrometer 108. For example, the low pressure can be created by a vacuum pump attached to the mass spectrometer 108. In some implementations, prior to the mass spectrometer, the analyte may be collected and delivered to an ion optic system. In some instances, the ion optic system may be configured to filter neutral species in the analyte, to allow ions passing through, and to eliminate contamination of the mass spectrometer 108. In some implementations, the mass spectrometer 108 may include a mass selector and a mass analyzer, which are configured to separate and identify the ionization products in the ionized analyte according to their mass-to-charge (m/z) ratio. In some implementations, the mass spectrometer 108 may output a set of mass spectra (e.g., intensity of the ionized product vs. the m/z ratio) to the computer system 102, which may be stored in the memory 122, analyzed by running a program 126 and results may be further displayed on the display 130. In some implementations, the mass spectrometer 108 may be implemented as the mass spectrometer 230 as shown in FIG. 2 or in different manner.

In some implementations, some of the processes and logic flows described in this specification can be automatically performed by one or more programmable processors, e.g. processor 120, executing one or more computer programs to perform actions by operating on input data and generating output. For example, the processor 120 can run the programs 126 by executing or interpreting scripts, functions, executables, or other modules contained in the programs 126. In some implementations, the processor 120 may perform one or more of the operations described, for example, with respect to FIG. 5.

In some implementations, the processor 120 can include various kinds of apparatus, devices, and machines for processing data, including, by way of example, a programmable data processor, a system on a chip, or multiple ones, or combinations, of the foregoing. In certain instances, the processor 120 may include special purpose logic circuitry, e.g., an Arduino board, an FPGA (field programmable gate array), an ASIC (application specific integrated circuit), or a Graphics Processing Unit (GPU) for running the deep learning algorithms. In some instances, the processor 120 may include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. In some examples, the processor 120 may include, by way of example, both general and special purpose microprocessors, and processors of any kind of digital computer.

In some implementations, the processor 120 may include both general and special purpose microprocessors, and processors of any kind of quantum or classic computer. Generally, a processor 120 receives instructions and data from a read-only memory or a random-access memory or both, e.g., memory 122. In some implementations, the memory 122 may include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD ROM and DVD-ROM disks. In some cases, the processor 120 and the memory 122 can be supplemented by, or incorporated in, special purpose logic circuitry.

In some implementations, the data 124 stored in the memory 122 may include, operational parameters, a standard reference database and output data. In some instances, the standard reference database includes a mass spectral reference library, which may be used for identification of unknow microorganisms. In some implementations, the programs 126 can include software applications, scripts, programs, functions, executables, or other modules that are interpreted or executed by the processor 120. In some implementations, the programs 126 may include machine-readable instructions for performing deep learning algorithms. In some instances, the programs 126 may include machine-readable instructions for delivering the liquid solvent to the sampling probe, and collecting the analyte from the sampling probe. In some instances, the programs 126 may obtain input data from the memory 122, from another local source, or from one or more remote sources (e.g., via a communication link). In some instances, the programs 126 may generate output data and store the output data in the memory 122, in another local medium, or in one or more remote devices (e.g., by sending the output data via the communication network 106). In some examples, the programs 126 (also known as, software, software applications, scripts, or codes) can be written in any form of programming language, including compiled or interpreted languages, declarative or procedural languages. In some implementations, the programs 126 can be deployed to be executed on the computer system 102.

In some implementations, the communication interface 128 may be connected to a communication network, which may include any type of communication channel, connector, data communication network, or other link. In some instances, the communication interface 128 may provide communication with other systems or devices. In some instances, the communication interface 128 may include a wireless communication interface that provides wireless communication under various wireless protocols, such as, for example, Bluetooth, Wi-Fi, Near Field Communication (NFC), GSM voice calls, SMS, EMS, or MMS messaging, wireless standards (e.g., CDMA, TDMA, PDC, WCDMA, CDMA2000, GPRS) among others. In some examples, such communication may occur, for example, through a radio-frequency transceiver or another type of component. In some instances, the communication interface 128 may include a wired communication interface (e.g., USB, Ethernet) that can be connected to one or more input/output devices, such as, for example, a keyboard, a pointing device, a scanner, or a networking device such as a switch or router, for example, through a network adapter.

In some implementations, the communication interface 128 can be coupled to input devices and output devices (e.g., the display device 130, the input device 132, or other devices) and to one or more communication links. In the example shown, the display device 130 is a computer monitor for displaying information to the user or another type of display device. In some implementations, the input device 132 is a keyboard, a pointing device (e.g., a mouse, a trackball, a tablet, and a touch sensitive screen), or another type of input device, by which the user can provide input to the computer system 102. In some examples, the computer system 102 may include other types of input devices, output devices, or both (e.g., mouse, touchpad, touchscreen, microphone, motion sensors, etc.). The input devices and output devices can receive and transmit data in analog or digital form over communication links such as a wired link (e.g., USB, etc.), a wireless link (e.g., Bluetooth, NFC, infrared, radio frequency, or others), or another type of link.

In some implementations, other kinds of devices may be used to provide interaction with a user as well; for example, feedback provided to the user can be any form of sensory feedback, e.g., visual feedback, auditory feedback, or tactile feedback; and input from the user can be received in any form, including acoustic, speech, or tactile input. For example, the sampling probe 104 may contain a control element (e.g., button, pedal, etc.) which may be used as a controller to initiate, interrupt, restart, or terminate a detection process (e.g., the pedal 226 as shown in FIG. 2). In some instances, a graphic user interface (GUI) may be used to provide interactions between a user and the microorganism identification system 100. In certain instances, the GUI may be communicably coupled to the computer system 102. For example, when the control system 106 is activated (e.g., by pushing on the pedal 226 in FIG. 2), the GUI can initiate an analysis process in the mass spectrometer 108. For example, when the analysis process is completed, the GUI can output a report with analysis results.

FIG. 2 is a schematic diagram showing aspects of an example microorganism identification system 200. In the example shown in FIG. 2, the example system 200 includes a sampling probe 202, a control system 204, and a mass spectrometer 230. As shown in FIG. 2, the sampling probe 202 is coupled between the control system 204 and the mass spectrometer 230 through transfer tubes 206A, 206B. In some examples, the example system 200 may include additional or different components, and the components may be arranged as shown or in another manner.

In the example shown in FIG. 2, the sampling probe 202 includes a housing 208A and a probe tip 208B. In some implementations, the housing 208A may provide a grip for being used as a handheld sampling probe. In some implementations, the housing 208A may include a control element, e.g., a trigger or button. For example, the control element may be used to control the liquid solvent transferring through the sampling probe 202. In some instances, the control element may be separated from the housing 208A, e.g., configured as a foot pedal. For another example, the control element may be coupled to a mechanism which may be used to eject the probe tip 208B. In some implementations, the sampling probe 202 may be composed of materials, such as synthetic polymers that are biologically compatible and resistant to chemicals used in the measurement. For example, the materials for the sampling probe 202 may be compatible with a variety of liquid solvent (e.g., polar or non-polar) that is used for extracting and carrying an analyte to the mass spectrometer 230. In some examples, the synthetic polymers that may be used for fabricating the sampling probe 202 may include Polydimethylsiloxane (PDMS), or Polytetrafluoroethylene (PTFE). In some implementations, the probe tip 208B may use the same material as the housing 208A, different materials or different compositions.

In some implementations, the sampling probe 202 may be manufactured using a 3D printing process, a machining process or another process. In some implementations, the housing 208A of the sampling probe 202 may include two internal channels which are fluidically coupled with respective transfer tubes 206A, 206B and respective channels in the probe tip 208B. In some implementations, the transfer tubes 206A, 206B are configured for supplying a liquid solvent from the control system 204 to the probe tip 208B and to obtain an analyte by collecting at least a portion of the liquid solvent with suspended microorganisms from the probe tip 208B. The sampling probe 202 may also include a gas channel (e.g., an open port that receives air from the surrounding atmosphere) that allows liquid to be flushed from the sampling probe 202, for example, between uses or at other instances.

In some implementations, the probe tip 208B may be detachable from the housing 208A, which can be disposed and replaced if contaminated, e.g., after a certain number (e.g., one or more) of regular uses or when switching between different samples. In some cases, the probe tip 208B may include internal channels that are fluidically coupled to the respective channels in the housing 208A and further to the respective transfer tubes 206A, 206B. In some implementations, the probe tip 208B may be integrated with the housing 208A as a monolithic structure. In some implementations, the probe tip 208B may be implemented as the probe tip 302 as shown in FIG. 3 or in another manner.

The example sampling probe 202 shown in FIG. 2 can directly sample biospecimens without forming biohazardous aerosols or microdroplets. For example, the sample probe 202 can form a liquid analyte on a sample surface, and extract the liquid analyte from the sample surface, without applying any voltage to the sample surface, and without energizing the surface in any other manner (e.g., without energizing the sample surface using electrical, optical, mechanical, vibrational or other energy sources). As such, the liquid analyte is formed and collected without producing microdroplets or aerosols in the atmosphere or open environment around the sample surface and the sampling probe 202.

The example sampling probe 202 shown in FIG. 2 can be used for the rapid and direct analysis of microorganisms. For example, in some experiments, the sampling probe 202 was able to identify several clinically relevant bacterial species in less than 30 seconds, with high accuracy and minimal sample preparation. In these experiments, statistical classifiers were generated using the least absolute shrinkage and selection operator for Gram type, genus, and species average accuracy of 93.3% in training and validation sets. These results demonstrate the capability of the sampling probe 202 to differentiate bacteria at different taxonomical levels rapidly, with no sample preparation.

The example sampling probe 202 shown in FIG. 2 requires no sample preparation, harsh solvents, or applied voltages to detect and identify microorganisms. For instance, no sample preparation, harsh solvents, or applied voltages were used in the rapid differentiation of bacteria from Gram type to species level differentiation of eight bacterial species: *Staphylococcus aureus* (*S. aureus*), *Staphylococcus epidermidis* (*S. epidermidis*), *Streptococcus pyogenes* (Group A *Strep.*), *Streptococcus agalactiae* (Group B *Strep.*), *Kingella kingae* (*K. kingae*), *Pseudomonas aeruginosa* (*P. aeruginosa*), *Escherichia coli* (*E. coli*), and *Salmonella enterica* (*S. enterica*).

In some implementations, the control system 204 may include a solvent container and a mechanical pumping system 228. In some instances, the mechanical pumping system 228 may contain one or more mechanical pumps. In some instances, the one or more mechanical pumps may be programable. In certain examples, the one or more mechanical pumps may be controlled by a computer system, e.g., the computer system 102 in FIG. 1. In some implementations, a mechanical pump may be a syringe pump, a peristatic pump or other type of pump, which can provide high-precision, microfluidic dispensation of the liquid solvent to the probe tip 208B, e.g., the internal reservoir 318 of the probe tip 302 as shown in FIG. 3. In some implementations, each of the one or more mechanical pumps may be equipped with separate solvent containers containing different types of liquid solvents. In some instances, different types of liquid solvents may be selected or mixed according to the types of microorganisms and initial measurement results. For example, bacteriolytic enzymes may be added to and mixed with the liquid solvent for cell lysis and extraction of intercellular molecules. For another example, the bacteriolytic enzymes may be applied to the microorganisms on the sample surface before being suspended in the liquid solvent. In the example shown in FIG. 2, the liquid solvent in a container (e.g., syringe) can be delivered to the sampling probe 202 through a first transfer tube 206A. In some implementations, the control system 204 may supply a controlled volume of liquid solvent to the sampling probe 202 at a controlled flow rate according to the design of the probe tip 208B, e.g., the volume of the internal reservoir 318 as shown in FIG. 3.

As shown in FIG. 2, the control system 204 further includes one or more valves on the transfer tubes 206A, 206B. In some implementations, each of the one or more valves is configured to control a fluidic flow (e.g., start or stop a fluidic flow) in respective transfer tubes. In some implementations, each of the one or more valves may be mechanically activated and electrically controlled by a computer system, e.g., the computer system 102 as shown in FIG. 1. In some examples, the one or more valves 210 may include a pinch valve, a squeeze valve, other type of valve, or a combination. In some instances, the valve 210 on a second transfer tube 206B is a high-speed actuated pinch valve for controlling aspiration and extraction of the analyte to the ionization system 220. In some instances, the control system 204 is communicably coupled with a control unit 224. In some instances, the control unit 224 may include an Arduino board to control motions of the mechanical pumping system 228 and the one or more valves 210. As shown, the control unit 224 can be activated by pushing a pedal 226 and deactivated by releasing the pedal 226. In some instances, when activated, the control unit 224 may also initiate a data collection process performed by the mass spectrometer 230.

In some implementations, the transfer tubes 206A, 206B may have an inner diameter of 0.8 mm and may be made of biocompatible synthetic polymers, e.g., polytetrafluoroethylene (PTFE). In some implementations, the transfer tubes 206A, 206B may have a length in the range of approximately half a meter to one or more meters (e.g., a length in the range of approximately 0.5 m to 1.5 m, or in another range) to allow free handheld use of the sampling probe 202 by an operator without geometrical or spatial constraints.

In some implementations, the analyte may be collected and delivered to an ion optic system prior to the mass spectrometer 230. In some instances, the ion optic system may be configured to filter neutral species in the analyte, to allow ions passing through, and to eliminate contamination to the mass spectrometer 230.

In some implementations, the mass spectrometer 230 may include a mass selector and a mass analyzer. In some implementations, the mass selector may separate charged biomolecules extracted from the microorganisms according to their mass-to-charge (m/z) ratio based on dynamics of charged particles in electric and magnetic field in vacuum. The mass analyzer may include a set of electrodes that trap charged molecules using an electric field. The mass analyzer may use the electric field to control the oscillation path. This oscillation path can be detected and used to calculate the ratio of charge to mass for charged biomolecules. In some examples, the mass analyzer may output a set of mass spectra (or mass spectrometry data in another format) for data analysis.

In some implementations, when an analysis is completed by the mass spectrometer 230, the mass spectrometer 230 may produce a report with analysis results including a type of microorganism identified. As such, data from the mass spectrometer may be analyzed to detect, identify and classify microorganisms present at the sample surface (e.g., present on the exterior of the sample surface or within the sample). The analysis results may be used to guide clinical care, for example antibiotic therapy. In some instances, the data produced by the mass spectrometer 230 may be analyzed, and the results of the analysis can be used to determine an appropriate treatment for a patient. For instance, a database may be used to identify potential antibiotics (e.g., type and dosage) to be administered based on the level or type of microorganism identified from the mass spectrometer data. In some cases, the treatment can be administered to a patient during an ongoing medical procedure.

FIG. 3 is a schematic diagram showing aspects of a sampling probe 300 in an example microorganism identification system. As shown in FIG. 3, the sampling probe 300 includes a probe tip 302 and a housing 304. The example probe tip 302 includes one mandrel end 306 in a tapered cylindrical shape which is used for contacting a sample surface 320, and one cylindrical end 308 which is used to engage with a receiving end of the housing 304. In some implementations, the cylindrical end 308 may make an air-tight seal with the receiving end of the housing 304. In some examples, the probe tip 302 may include additional or different components, and the components may be arranged as shown or in another manner.

As shown in a cross-sectional view of the probe tip 302 in FIG. 3, the probe tip 302 includes three distinct internal channels, including a liquid supply channel 312, a liquid extraction channel 314, and a gas channel 316. In some implementations, the three internal channels 312, 314, 316 are aligned with respective internal channels (not shown) in the receiving end of the housing 304 to provide fluidic communication with transfer tubes. In some instances, the transfer tubes may be implemented as the transfer tubes 206A, 206B as shown in FIG. 2 or in another manner. In some implementations, the three internal channels 312, 314, 316 may be directly coupled with transfer tubes that extends through the housing 304 from the end opposite to the receiving end to the receiving end of the housing 304 or may be coupled with the transfer tubes in other manner to allow liquid and gas flow.

In some implementations, the housing 304 is configured to provide fluidic communication with a control system and a mass spectrometer through respective transfer tubes, e.g., the transfer tubes 206A, 206B as shown in FIG. 2. In some implementations, the housing 304 and the probe tip 302 may be composed of biologically compatible synthetic polymers. In some implementations, the housing 304 and the probe tip 302 may be fabricated using a 3D printing process, a machining process or another type of fabrication process.

In some implementations, the sample surface 320 may be a surface of a solid substrate. For example, the sample surface 320 may be a glass slide, a petri dish, or an agar plate. In some implementations, the sample surface 320 may make a liquid-tight seal with the mandrel end 306 of the probe tip 302 in order to prevent leakage of the liquid solvent from the internal reservoir 318. In some implementations, the sample surface 320 may contain microorganisms of interest. In some cases, the sample surface 320 is known to potentially contains microorganisms of interest, and the probe is used to collect a sample in order to determine whether the sample surface 320 does or does not contain microorganisms of interest.

In some implementations, the sample surface 320 can be or include the surface of a tissue sample, a bone sample, or another type of biological sample. For example, the sample surface 320 can be an in-vivo or ex-vivo tissue site. In some cases, the sampling probe 300 is used during a medical procedure (e.g., during surgery) to evaluate a sample site of a subject. In a surgery environment, the solvent can be or include water, ethanol mixed with water, or another type of solvent. The sampling probe 300 may collect samples from tissue exposed during a surgical procedure in order to determine whether bacteria or another microorganism is present at the tissue site. The sample obtained by the probe 300 may be analyzed by a mass spectrometer to identify and classify the bacteria, which may be used to prescribe treatment or therapy.

In some aspects of operation, the liquid supply channel 312 receives the liquid solvent from an external container, guides the liquid solvent to the internal reservoir 318 at the probe tip 302, where the liquid solvent may be in direct contact with the sample surface 320, and fills at least a portion of the internal reservoir 318 with the liquid solvent. The liquid supply channel 312 may provide a first internal pathway 332 in the probe tip. In some implementations, the liquid solvent may be received from the external container as a part of a control system, e.g., the syringe pump as shown in FIG. 2 or another type of mechanical pumping system.

In some implementations, the internal reservoir 318 may have a cylindrical shape and be coupled to the liquid supply channels 312. In certain examples, the liquid solvent received from the liquid supply channel 312 in the internal reservoir 318 makes direct contact with the sample surface 320. The sample surface 320 may include an outer surface that is directly exposed to the fluid in the internal reservoir 318, and the sample surface 320 may include additional layers or other material beneath the outer surface; biomolecules from the outer surface or from material beneath the outer surface may be extracted into the fluid in the internal reservoir 318. In some instances, at least a portion of the microorganism cells from the sample surface 320 may be suspended, and biomolecules from microorganism cells may be extracted into the liquid solvent to form the liquid analyte. In some implementations, the diameter 322 of the internal reservoir 318 is determined by, for example, the size of the sample surface 320 and the amount of the microorganisms on the sample surface 320. In some instances, the diameter 322 and height 324 of the internal reservoir 318 may determine the volume of the liquid solvent exposed to the sample surface 320 and performance aspects of the chemical measurement system, for example a spatial resolution, limit of detection, and accuracy. In some instances, the diameter of the internal reservoir 318 of the probe tip 302 may be in a range of 1.5-5.0 mm. For example, when the diameter 322 of the internal reservoir is 2.77 mm and the height 324 of the internal reservoir 318 is 1.7 mm, the volume of a liquid solvent that is contained in the internal reservoir 318 is 10 microliter (μL). For another example, when the diameter of the internal reservoir 318 is 1.5 mm and the height 324 is 2.5 mm, the volume of a liquid solvent that is contained in the internal reservoir 318 is 4.4 μL. The internal reservoir 318 may have a different shape, aspect ratio, size or dimension.

In some instances, the liquid extraction channel 314 provides a second, distinct internal pathway 334 in the probe tip 302. In some aspects of operation, the liquid extraction channel 314 obtains an analyte by extracting at least a portion of the liquid solvent carrying the suspended cells or the extracted biomolecules from the internal reservoir 318, and guides the analyte to the transfer tube that is coupled to a mass spectrometer. In some implementations, the analyte from the internal reservoir 318 may be extracted by a vacuum pump coupled to the mass spectrometer (e.g., the mass spectrometer 230 as shown in FIG. 2). In some implementations, a low pressure created on one end of the transfer tube may facilitate liquid aspiration to drive the analyte from the internal reservoir 318 to the mass spectrometer through the liquid extraction channel 314.

In some implementations, the gas channel 316 provides a third, distinct internal pathway 336 in the probe tip 302. In some instances, the gas channel 316 is configured for preventing collapse of the sampling probe, transfer tubes and the control system during the extraction. In some instances, the gas channel 316 is open to atmosphere (e.g., air). In some instances, diameters of the liquid supply channel 312, the liquid extraction channel 314 and the gas channel 316 may be equal to 0.8 mm. Gas from the gas channel 316 may be used to push the liquid out of the liquid extraction channel 314 to the mass spectrometer.

Figure 4A:
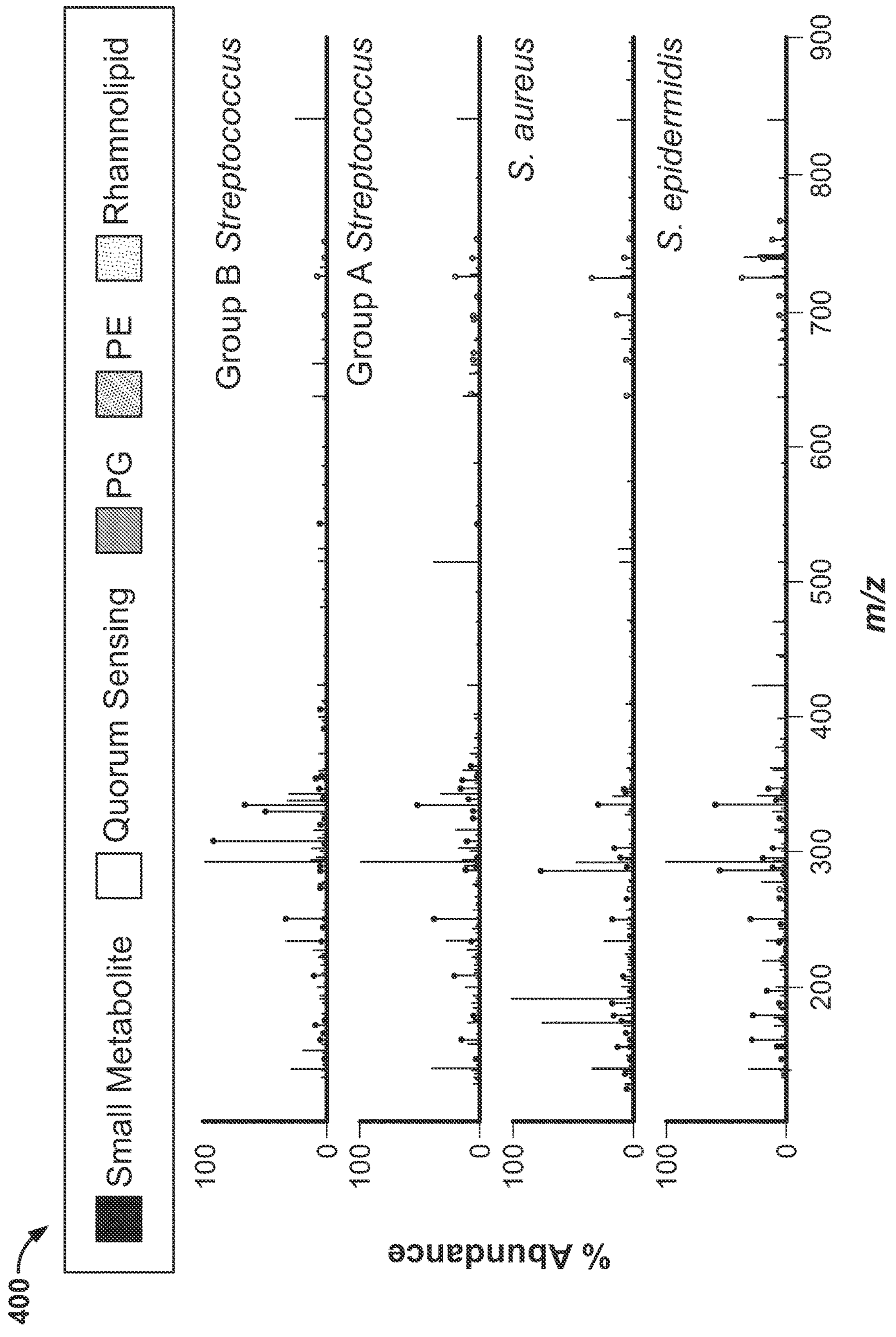
FIGS. 4A-4B are example mass spectra of eight types of bacteria.
Figure 4B:
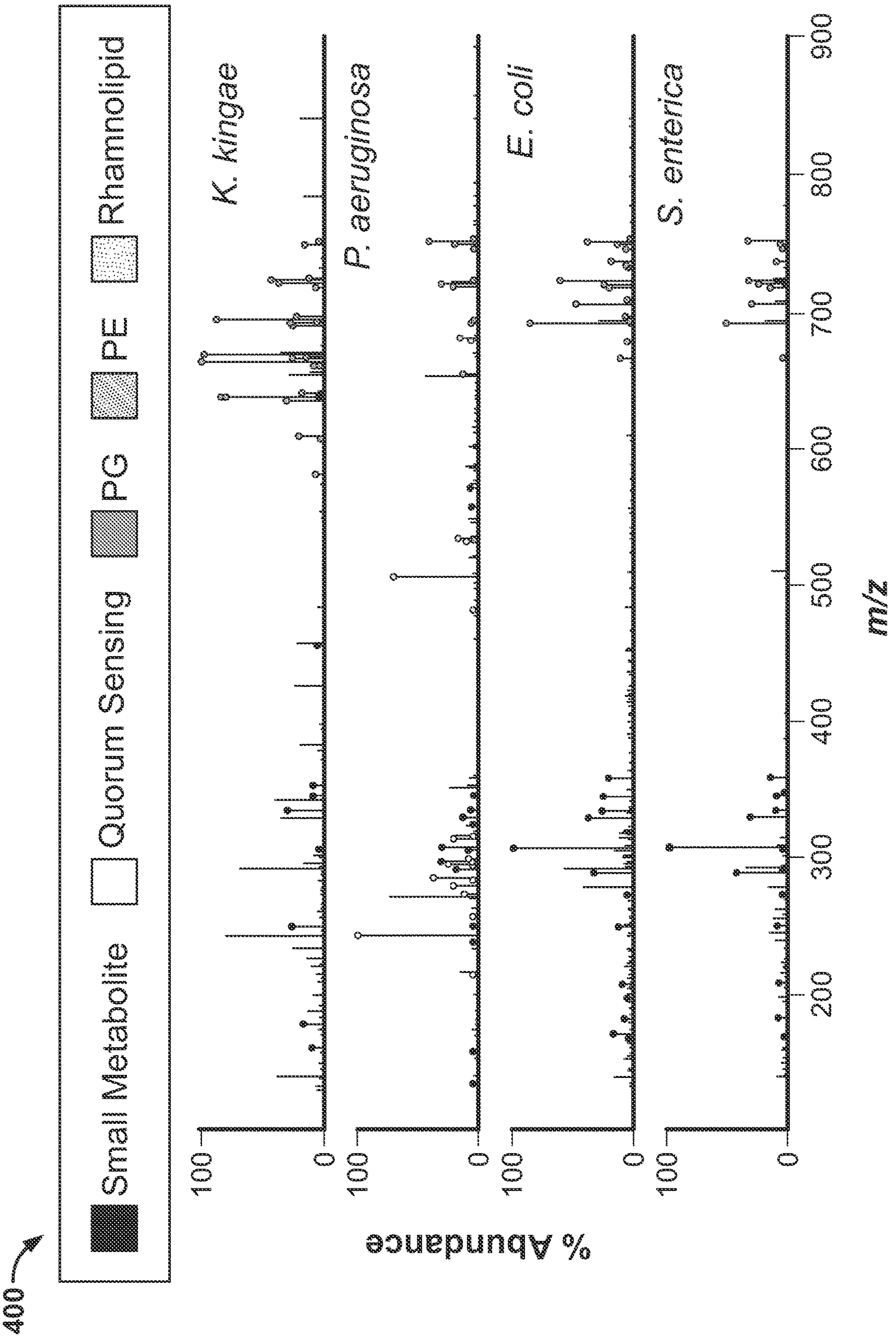

FIG. 4A-4B are example mass spectra 400 of eight types of bacteria. As show in FIGS. 4A-4C, the eight types of bacteria include *Streptococcus* (*Str.*) *agalactiae* ($n_{strain}$=5), *Str. pyogenes* ($n_{strain}$=5), *Staphylococcus* (*S.*) *aureus* ($n_{strain}$=6), *S. epidermidis* ($n_{strain}$=4), *Pseudomonas* (*P.*) *aeruginosa* ($n_{strain}$=6), *Escherichia* (*E.*) *coli* ($n_{strain}$=7), *Salmonella* (*S.*) *enterica* ($n_{strain}$=6), and *Kingella* (*K.*) *kingae* ($n_{strain}$=3). In the example shown in FIGS. 4A-4B, mass spectra may be collected by a microorganism identification system. In some implementations, a microorganism identification system may be used to classify and identify bacteria based on molecular profiles.

In some implementations, standard reference bacteria specimens may be obtained from American Type Culture Collection (ATCC) and BEI Resources. In certain instances, specimens may be streaked on blood agar plates or in another manner. In some examples, specimens may be further cultured overnight at a temperature of 37 degree Celsius in an incubator. Multiple colonies of the cultured bacteria can be formed on the blood agar plates. Each of the multiple colonies is then removed from the blood agar plates and spread onto a multi-well PTFE-coated glass slide using a sterile inoculating loop and analyzed using the microorganism identification system. The microorganism identification system may be implemented as the microorganism identification system as shown in FIGS. 1-2. In some examples, the microorganism identification system may include a sampling probe. In some instances, the sampling probe may be configured as the sampling probe 300 as shown in FIG. 3. The probe tip of the sampling probe has an internal reservoir with a dimeter of 2.7 mm.

In some instances, after the probe tip of the sampling probe is positioned against the glass slide as shown in FIG. 3, a fixed volume of the liquid solvent, e.g., water, for extracting biomolecules is delivered to the internal reservoir of the sampling probe. In some instances, the fixed volume of the liquid solvent in the internal reservoir is kept in direct contact with the bacterial smear for a time period, e.g., 3 seconds or another period of time, to extract biomolecules from the bacterial cells. After the first time period, the analyte is transferred from the internal reservoir to the mass spectrometer for analysis. In some implementations, the mass spectrometer of the microorganism identification system may include a ThermoFisher Q Exactive HF Hybrid Quadrupole-Orbitrap mass spectrometer operating in positive and negative ion modes in a mass-to-charge (m/z) range of 100-1200 with a resolving power of 120,000.

In some implementations, the multiple colonies may be analyzed in a random order to minimize batch effects. In some instances, analyses of the colonies from the same strain are treated as replicates, as these colonies have the same genetic material. In certain instances, analyses of different strains from the same species are treated as different samples, as species are defined as a group of related, distinct clonal strains.

In some implementations, a variety of molecular features in the mass spectra corresponding to the biomolecules extracted from the bacterial cells may be used to detect, differentiate, and classify bacteria. For example, the biomolecules extracted from the bacterial cells may include amino acids, dipeptides, quorum sensing molecules, fatty acids, and lipids. In some instances, peaks in the mass spectra at m/z=747.519 corresponding to phosphatidylglycerol 34:1 [M−H]− and peaks at m/z=719.488 corresponding to phosphatidylglycerol 32:1 [M−H]− may be also used as molecular features for identification and classification of bacteria.

As shown in FIGS. 4A-4B, qualitative differences in molecular profiles of these species may be observed in the mass spectra. For example, 12 tentatively identified alkylquinolone quorum sensing molecules were observed in *P. aeruginosa* including *Pseudomonas* quorum sensing signal (PQS) [M+Cl]− (m/z 294.127), heptyl-quinolone [M−H]− (m/z 242.115), and undecylquinolone (UDQ) [M−H]− (m/z 298.127). Several tentatively identified phospholipids were observed exclusively in *K. kingae* such as tentatively identified LPG 14:1 [M−H]− (m/z 455.241), PE 28:1 [M−H]− (m/z 632.430), and PE 28:0 [M−H]− (m/z 634.446). Ions tentatively identified as acetyl-methionine [M−H]− (m/z 190.052), PE 16:0_17:1 (m/z 702.509), PG 16:0_17:1 (m/z 733.503) were observed in the enterobacteria *E. coli* and *S. enterica* but not other Gram negative species. Molecules with relative abundances that differed between *Streptococcus* species *Str. agalactiae* and *Str. pyogenes* include glutathione [M−H]− (m/z 306.077) and the tripeptide Gly-Ser-Glu [M−H]− (m/z 272.089). Additionally, molecules with relative abundances that differed between *Staphylococcus* species *S. aureus* and *S. epidermidis* include acetyl-aspartic acid [M−H]− (m/z 174.040) and acetyl-tyrosine [M−H]− (m/z 222.076), which were at a significantly higher relative abundance in *S. epidermidis*, and pentose phosphate [M−H]− (m/z 421.075), hydroxymethylpyridine dicarboxylate [M−H]− (m/z 196.025) which were at a significantly higher relative abundance in *S. aureus*. In some implementations, an abundance of some PG lipids may be used as an indicator of Gram-positive outer membranes in the bacteria and an abundance of PE (e.g., PE 14:0 (m/z=634.446)) may be used as an indicator of Gram-negative outer membranes in the bacteria.

FIGS. 5A-5E are schematic diagrams 500, 510, 520, 530, 540, and 550 showing prediction performance of example statistical models.

Figure 5A:
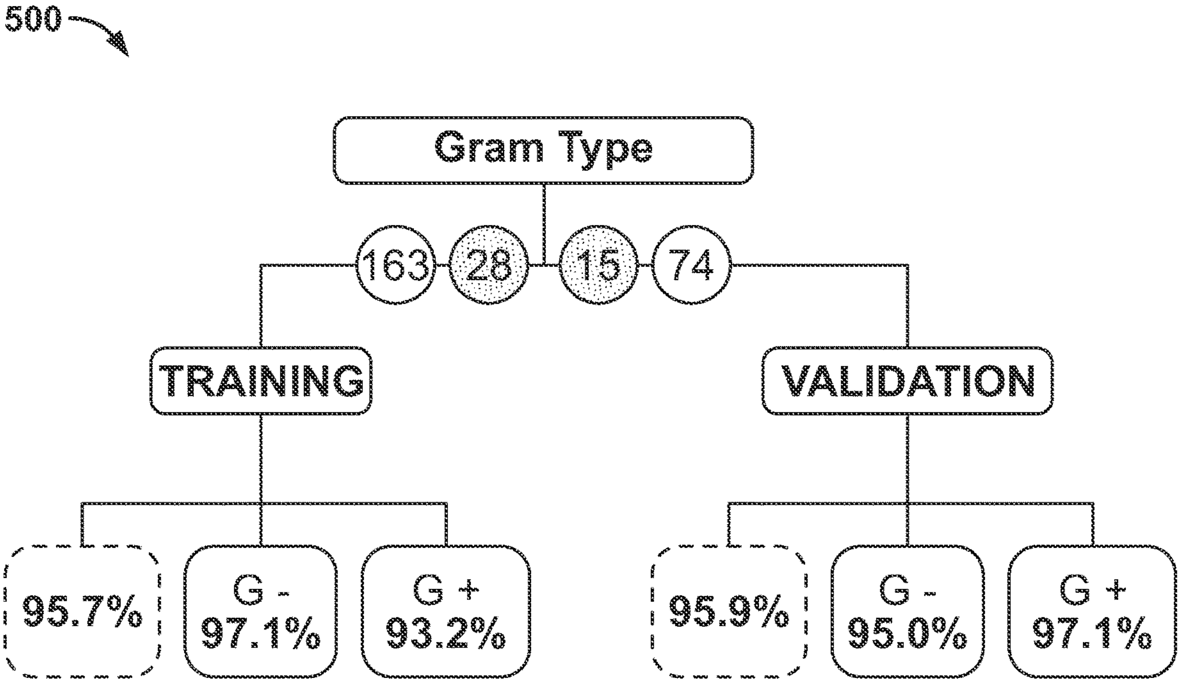
FIGS. 5A-5E are schematic diagrams showing prediction performance of example statistical models.

As shown in FIG. 5A, the statistical model is trained for discriminating bacteria based on Gram type, e.g., gram-negative (G−) and Gram-positive (G+) bacteria. The bacteria samples are divided in two sets, e.g., a training set with 163 mass spectra ($n_{total}$=163) and 28 strains ($n_{strain}$=28), and a validation set with 74 mass spectra ($n_{total}$=74) and 15 strains ($n_{strain}$=15). In some implementations, the mass spectrometry data is obtained and processed with respect to the processes described in FIGS. 4A-4B or in another manner. This statistical model performed with recalls (e.g., accuracy per type) of 97.1% and 93.2% for G− and G+ bacteria, respectively and an overall accuracy of 95.7% in the training set; and recalls of 95.0% and 97.1% for G− and G+ bacteria, respectively and an overall accuracy of 95.9% in the validation set.

Figure 5B:
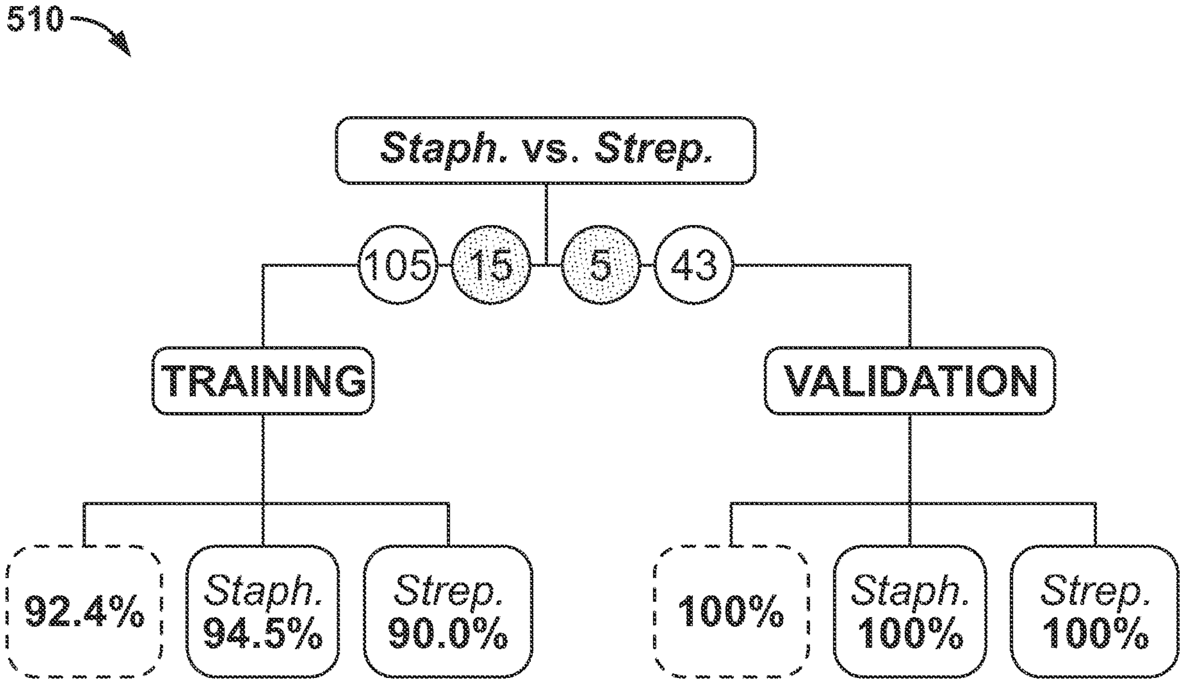

As shown in FIG. 5B, the example statistical model is trained for discriminating bacteria species, e.g., *Staphylococcus* (*Staph.*) vs. *Streptococcus* (*Strep.*). The bacteria samples are divided in two sets, e.g., a training set with 105 analysis ($n_{total}$=105) and 15 strains ($n_{strain}$=15), and a validation set with 43 analysis ($n_{total}$=43) and 5 strains ($n_{strain}$=5). In some implementations, the mass spectrometry data is obtained and processed with respect to the processes described in FIGS. 4A-4B or in another manner. This statistical model performed with recalls (e.g., accuracy per type) of 94.5% and 90.0% for *Staph.* and *Strep.*, respectively and an overall accuracy of 92.4% in the training set; and recalls of 100% and 100% for *Staph*. and *Strep*., respectively and an overall accuracy of 100% in the validation set.

For the example statistical models for discriminating gram type and *Staph*. vs. *Strep* species shown in FIGS. 5A, 5B, four analyses of *Streptococcus gordonii* were used as an independent test set to evaluate the model performance on a species that was not present in the training set. The correct classification of *Streptococcus gordonii* by the example statistical models despite no representation of this species in the training sets indicates that the statistical models can be generalizable to other species that are not in training sets. In some instances, the methods and techniques presented here can reduce burden of creating statistical models and the complications with evolving organisms/new strains.

Figure 5C:
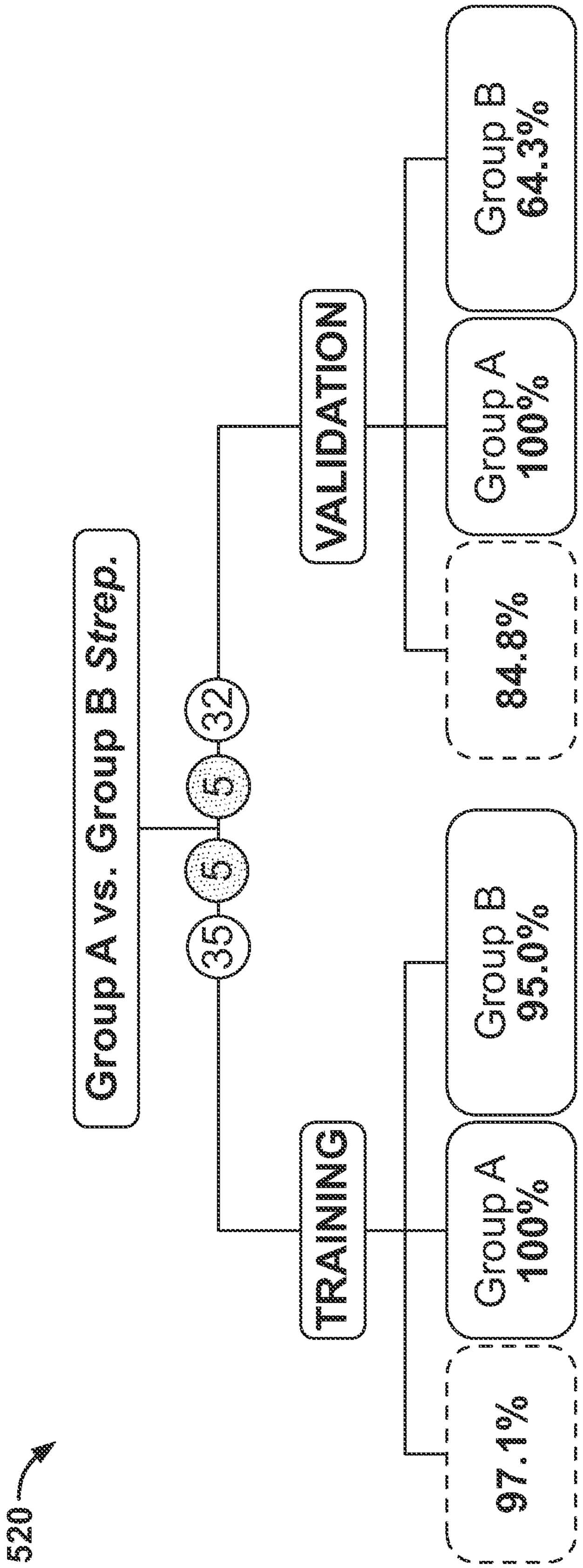

As shown in FIG. 5C, the example statistical model is trained for discriminating different groups of *Streptococcus*, e.g., Group A vs. Group B *Streptococcus*. The bacteria samples are divided in two sets, e.g., a training set with 35 analysis ($n_{total}$35) and 5 strains ($n_{strain}$=5), and a validation set with 32 analysis ($n_{total}$=32) and 5 strains ($n_{strain}$=5). In some implementations, the mass spectrometry data is obtained and processed with respect to the processes described in FIGS. 4A-4B or in another manner. This statistical model performed with recalls (e.g., accuracy per type) of 100% and 95.0% for Group A and Group B, respectively and an overall accuracy of 97.1% in the training set; and recalls of 100% and 64.3% for Group A and Group B, respectively and an overall accuracy of 84.8% in the validation set.

Figure 5D:
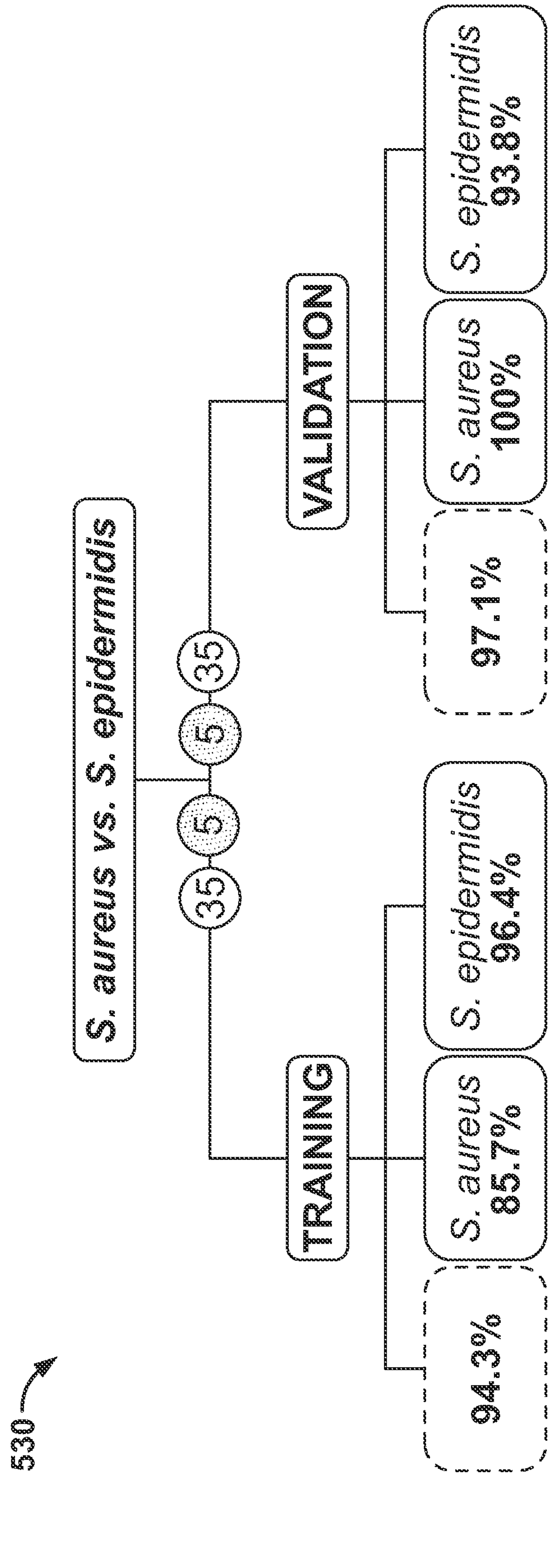

As shown in FIG. 5D, the example statistical model is trained for discriminating different *Staphylococcus* species, e.g., *S. aureus* vs. *S. epidermidis*. The bacteria samples are divided in two sets, e.g., a training set with 35 analysis ($n_{total}$=35) and 5 strains ($n_{strain}$=5), and a validation set with 35 analysis ($n_{total}$=35) and 5 strains ($n_{strain}$=5). In some implementations, the mass spectrometry data is obtained and processed with respect to the processes described in FIGS. 4A-4B or in another manner. This statistical model performed with recalls (e.g., accuracy per type) of 85.7% and 96.4% for *S. aureus* and *S. epidermidis*, respectively and an overall accuracy of 94.3% in the training set; and recalls of 100% and 93.8% for *S. aureus* and *S. epidermidis*, respectively and an overall accuracy of 97.1% in the validation set.

Figure 5E:
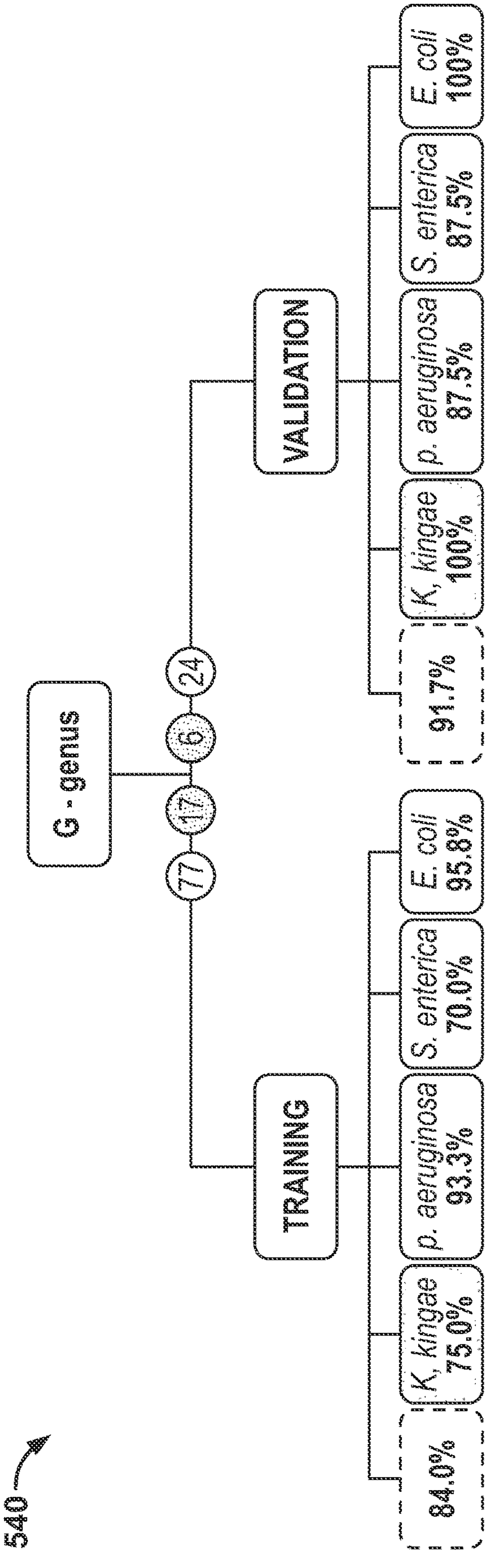

As shown in FIG. 5E, the example statistical model is trained for discriminating different Gram-negative species, e.g., *K. kingae, P. aeruginosa, S. enterica*, and *E. coli*. The bacteria samples are divided in two sets, e.g., a training set with 77 analysis ($n_{total}$=77) and 17 strains ($n_{strain}$=17), and a validation set with 24 analysis ($n_{total}$=24) and 6 strains ($n_{strain}$=6). In some implementations, the mass spectrometry data is obtained and processed with respect to the processes described in FIGS. 4A-4B or in another manner. This statistical model performed with recalls (e.g., accuracy per type) of 75.0%, 93.3%, 70.0% and 95.8% for *K. kingae, P. aeruginosa, S. enterica*, and *E. coli*, respectively and an overall accuracy of 84.0% in the training set; and recalls of 100%, 87.5%, 87.5%, and 100% for *K. kingae, P. aeruginosa, S. enterica*, and *E. coli*, respectively and an overall accuracy of 91.7% in the validation set.

FIGS. 6A-6E are plots 600, 610, 620, 630, 640, and 650 showing molecular ion peaks and statistical weights associated with the molecular ion peaks in the example statistical models.

Figure 6A:
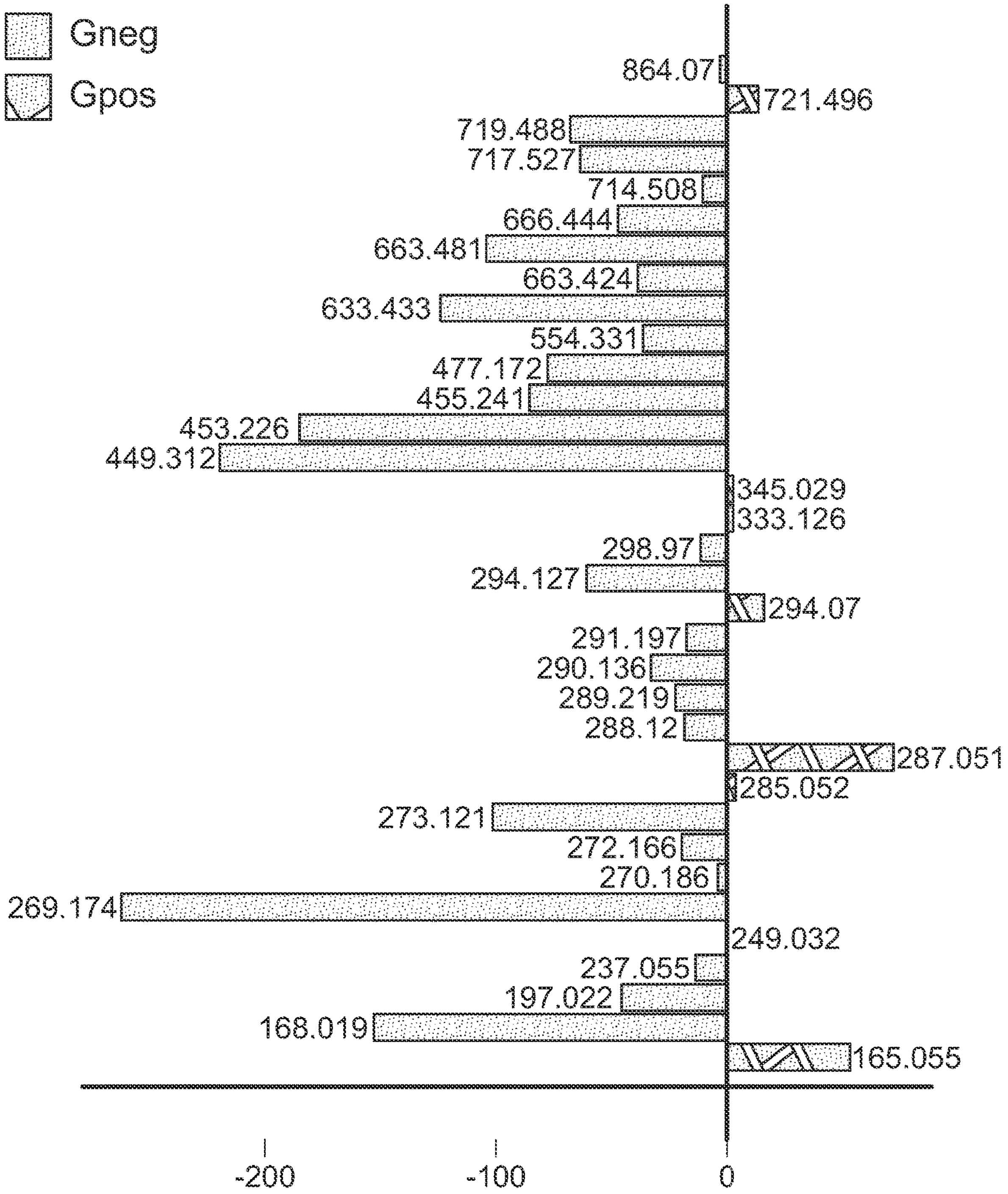
FIGS. 6A-6E are plots showing molecular ion peaks and statistical weights associated with the molecular ion peaks in the example statistical models.

As shown in FIG. 6A, the statistical model is trained for discriminating bacteria based on Gram type, e.g., gram-negative (G−) and Gram-positive (G+) bacteria. In some instances, the molecular ion peaks and the respective statistical weights are selected by the statistical model based on mass spectrometry profiles collected from a training set of banked tissue samples. 34 predictive features, which were selected by the statistical model, include tentatively identified small metabolites and phospholipids. Molecular ion peaks which are selected by the statistical model that are weighted toward classification of G− bacteria are located at m/z=168.019, 197.022, 237.055, 269.174, 270.186, 272.166, 273.121, 288.12, 289.219, 290.136, 291.197, 294.127, 298.97, 449.312, 453.226, 455.241, 477.172, 554.331, 633.433, 633.424, 663.481, 666.444, 714.508, 717.527, 719.488, and 864.07. Molecular ion peaks which are selected by the statistical model that are weighted toward classification of G+ bacteria are located at m/z=165.055, 249.032, 285.052, 287.051, 294.07, 333.126, 345.029, and 721.496.

Tentatively identified features weighted towards G− bacteria include ureidoglycine $[M+Cl]^-$ (m/z 168.020) and deoxycytidine phosphate (dCDP) $[M-H]^-$ (m/z 386.017) and phospholipids lyso-PG 14:1 $[M-H]^-$ (m/z 455.241), PG 14:0_14:1/12:0_16:1 $[M-H]^-$ (m/z 663.424), and PE 16:1_18:1 $[M-H]^-$ (m/z 714.508). Tentatively identified features weighted towards G+ bacteria include phosphocholine $[M-H_2O-H]^-$ (m/z 165.055), orotidine $[M-H]^-$ (m/z 287.051), and glycineamideribotide (GAR) $[M-H]^-$ (m/z 285.052).

In some implementations, the statistical weights of the respective molecular ion peaks that are indicative of different tissue types may have different signs in the statistical model. For example, the statistical weights with negative values are indicative of G+ bacteria and the statistical weights with positive values are indicative of G− bacteria. In some implementations, the statistical weights may be configured in another manner according to the statistical model. The methods and systems presented here can be used for gram-type assessment or another application.

Figure 6B:
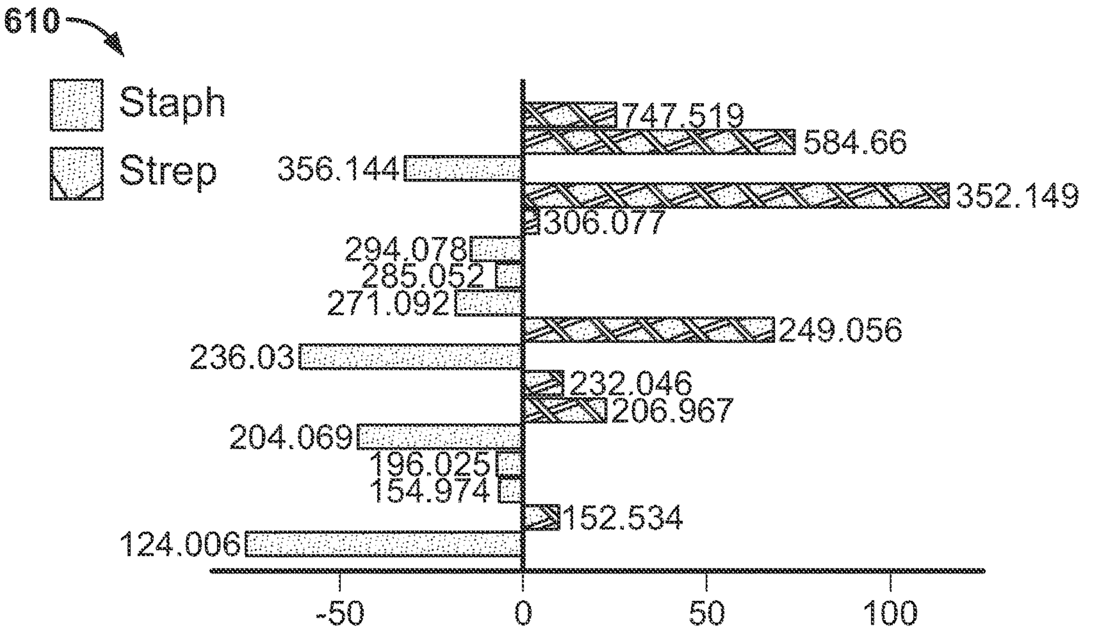

As shown in FIG. 6B, the example statistical model is trained for discriminating bacteria species, e.g., *Staphylococcus* (*Staph*.) vs. *Streptococcus* (*Strep*.). In some instances, the molecular ion peaks and the respective statistical weights are selected by the statistical model based on mass spectrometry profiles collected from a training set. 17 predictive features, which were selected by the statistical model, include tentatively identified small metabolites and phospholipids. Molecular ion peaks which are selected by the statistical model that are weighted toward classification of *Streptococcus* (*Strep*.) are located at m/z=152.534, 206.967, 232.046, 249.056, 306.077, 352.149, 584.66, and 747.519. Molecular ion peaks which are selected by the statistical model that are weighted toward classification of *Staphylococcus* (*Staph*.) are located at m/z=124.006, 154.974, 196.025, 204.069, 236.03, 271.092, 285.052, 294.078, and 356.144.

Tentatively identified features weighted towards *Staphylococcus* (*Staph*.) include tentatively identified taurine $[M-H]^-$ (m/z 124.006), glycerophosphoethanolamine $[M-2H+Na]^-$ (m/z 236.030), and tripeptide X $[M-H_2O-H]^-$ (m/z 356.144). Tentatively identified features weighted towards *Streptococcus* (*Strep*.) include phosphoglyceric acid $[M-2H+Na]^-$ (m/z 206.967), glutathione $[M-H]^-$ (m/z 306.077), tripeptide X $[M-H]^-$ (m/z 352.149), and PG 16:0_18:1 $[M-H]^-$ (m/z 747.519).

In some implementations, the statistical weights of the respective molecular ion peaks that are indicative of different tissue types may have different signs in the statistical model. For example, the statistical weights with negative values are indicative of *Streptococcus* (*Strep*.) and the statistical weights with positive values are indicative of *Staphylococcus* (*Staph.*). In some implementations, the statistical weights may be configured in another manner according to the statistical model.

Figure 6D:
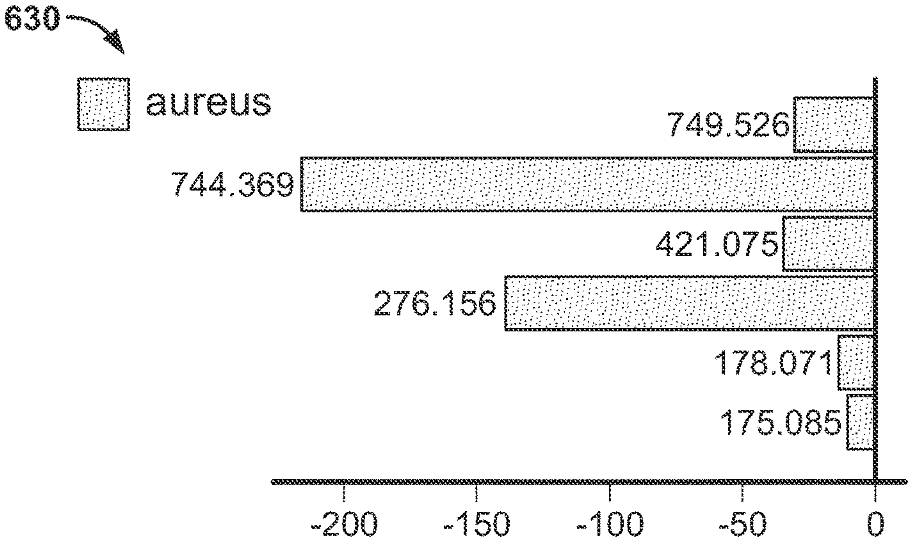
Figure 6E:
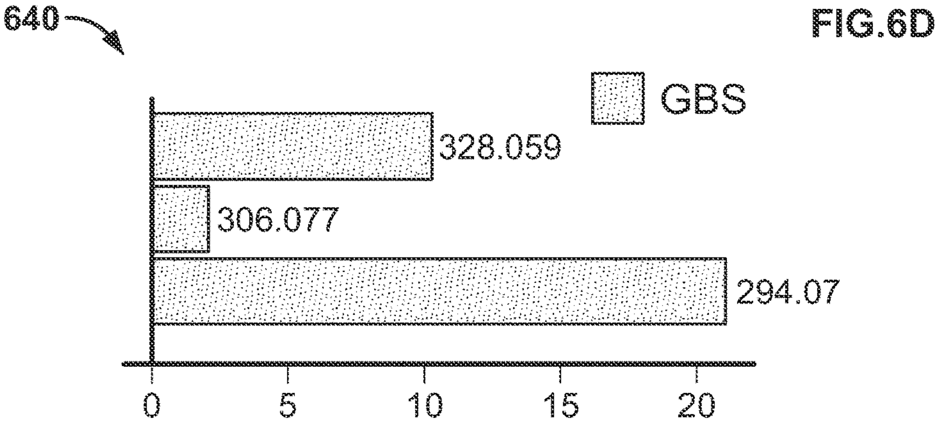
Figure 6C:
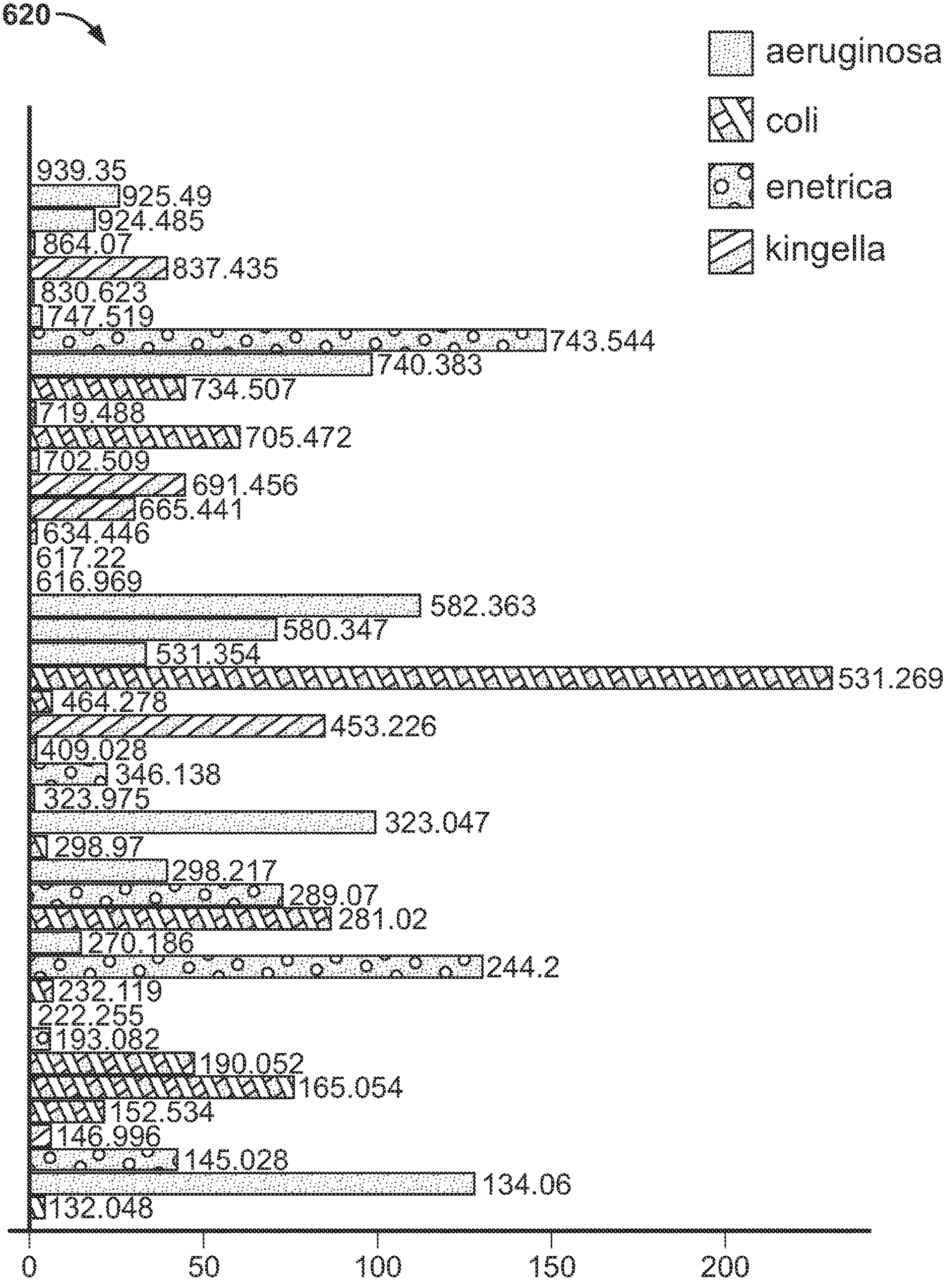

As shown in FIG. 6C, the example statistical model is trained for discriminating different Gram-negative species, e.g., *K. kingae, P. aeruginosa, S. enterica*, and *E. coli*. As shown in the plot 620, the molecular ion peaks and the respective statistical weights are selected by the statistical model based on mass spectrometry profiles collected from a training set. Forty-four features were selected for the model including 27 features that have been tentatively identified.

Molecular ion peaks which are selected by the statistical model that are weighted toward classification of *P. aeruginosa* are located at m/z=134.06, 270.186, 298.217, 323.047, 531.354, 580.347, 582.363, 740.383, 924.485, and 925.49. Molecular ion peaks which are selected by the statistical model that are weighted toward classification of *E. coli* are located at m/z=132.048, 152.534, 165.054, 190.052, 232.119, 281.02, 298.97, 464.278, 531.269, 705.472, 719.488, and 734.507. Molecular ion peaks which are selected by the statistical model that are weighted toward classification of *S. enterica* are located at m/z=145.028, 193.082, 244.2, 289.07, 346.138, 702.509, 743.544, and 747.519. Molecular ion peaks which are selected by the statistical model that are weighted toward classification of *K. kingae* are located at m/z=146.996, 453.226, 665.441, 691.456, and 837.435.

Tentatively identified features weighted towards *P. aeruginosa* include quorum sensing molecules PQS $[M+Cl]^-$ (m/z 294.127) and UDQ $[M-H]^-$ (m/z 298.128), pyochelin $[M-H]^-$ (m/z 323.053), and Rha-C12-C10 $[M-H]^-$ (m/z 531.534). Tentatively identified features weighted towards *K. kingae* include phospholipids PE 12:0_16:0/PE 14:0_14:0 $[M-H]^-$ (m/z 634.446), and PG 14:0_14:0 $[M-H]^-$, (m/z 665.441). Tentatively identified features weighed towards *S. enterica* include hexosamine $[M-H]^-$ (m/z 178.071), tripeptide X $[M-H]^-$ (m/z 346.142), and phospholipids PE 16:0_17:1 $[M-H]^-$ (m/z 702.509) and PG 16:0_18:1 $[M-H]^-$ (m/z 747.519). Tentatively identified features weighted towards *E. coli*. include lysophospholipids LPE 17:1 $[M-H]^-$ (m/z 464.278) and LPG 20:4 $[M-H]^-$ (m/z 455.241), acetyl-methionine $[M-H]^-$ (m/z 190.052), and PG 14:0_18:1/16:0_16:1 $[M-H]^-$ (m/z 719.488). The statistical weights for these predictive features have positive values.

As shown in FIG. 6D, the example statistical model is trained for discriminating different *Staphylococcus* species, e.g., *S. aureus* vs. *S. epidermidis*. As shown in the plot 630, the molecular ion peaks and the respective statistical weights are selected by the statistical model based on mass spectrometry profiles collected from a training set. 6 predictive features located at m/z=175.085, 178.071, 276.156, 421.075, 744.369, and 749.526 were selected by the statistical model and were all weighted towards *S. aureus*. Three of the predictive features have been tentatively identified as small metabolites and a glycerophospholipid including hexosamine $[M-H]^-$ (m/z 178.010), pentose phosphate $[M-H]^-$ (m/z 421.075), and C13 isotope of PG 16:0_18:1 $[M-H]^-$ (m/z 749.526). The statistical weights for these predictive features have positive values.

As shown in FIG. 6E, the example statistical model is trained for discriminating different groups of *Streptococcus*, e.g., Group A vs. Group B *Streptococcus*. As shown in the plot 640, the molecular ion peaks and the respective statistical weights are selected by the statistical model based on mass spectrometry profiles collected from a training set. 3 predictive features, which were selected by the statistical model, include tentatively identified small metabolites and phospholipids. Features weighted towards Group B *Strep.* include tentatively identified as fumarycarnitine $[M+Cl]^-$ (m/z 294.070), glutathione $[M-H]^-$ (m/z 306.077), and the dipeptide Lys-Pro $[M+Cl]^-$ (or glutathione+Na−2H)$^-$ (m/z 328.059). The statistical weights for these predictive features have negative values.

Figure 7A:
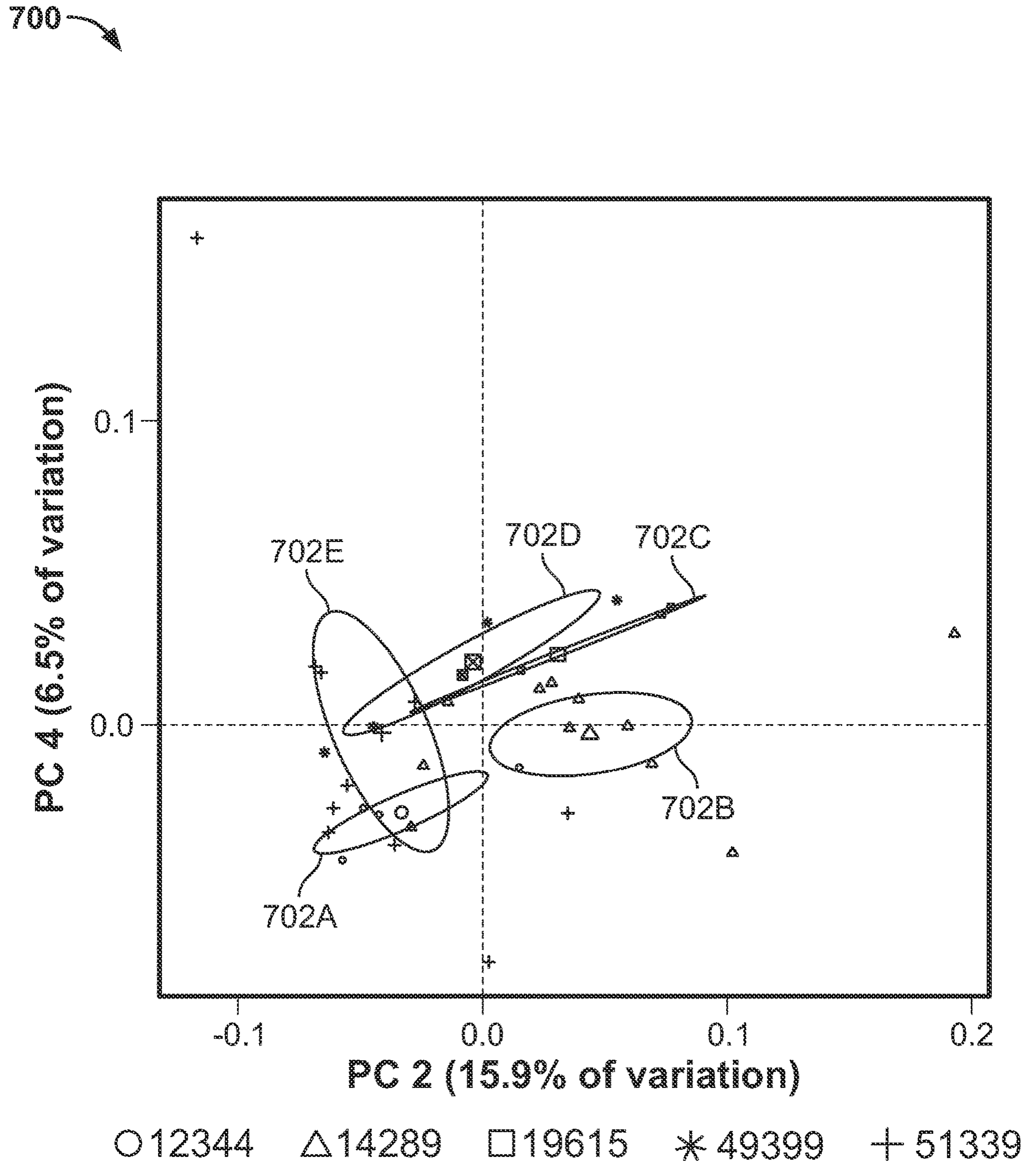
FIGS. 7A-7C are principle component analysis scatter plots showing clusters of samples based on their similarity.
Figure 7B:
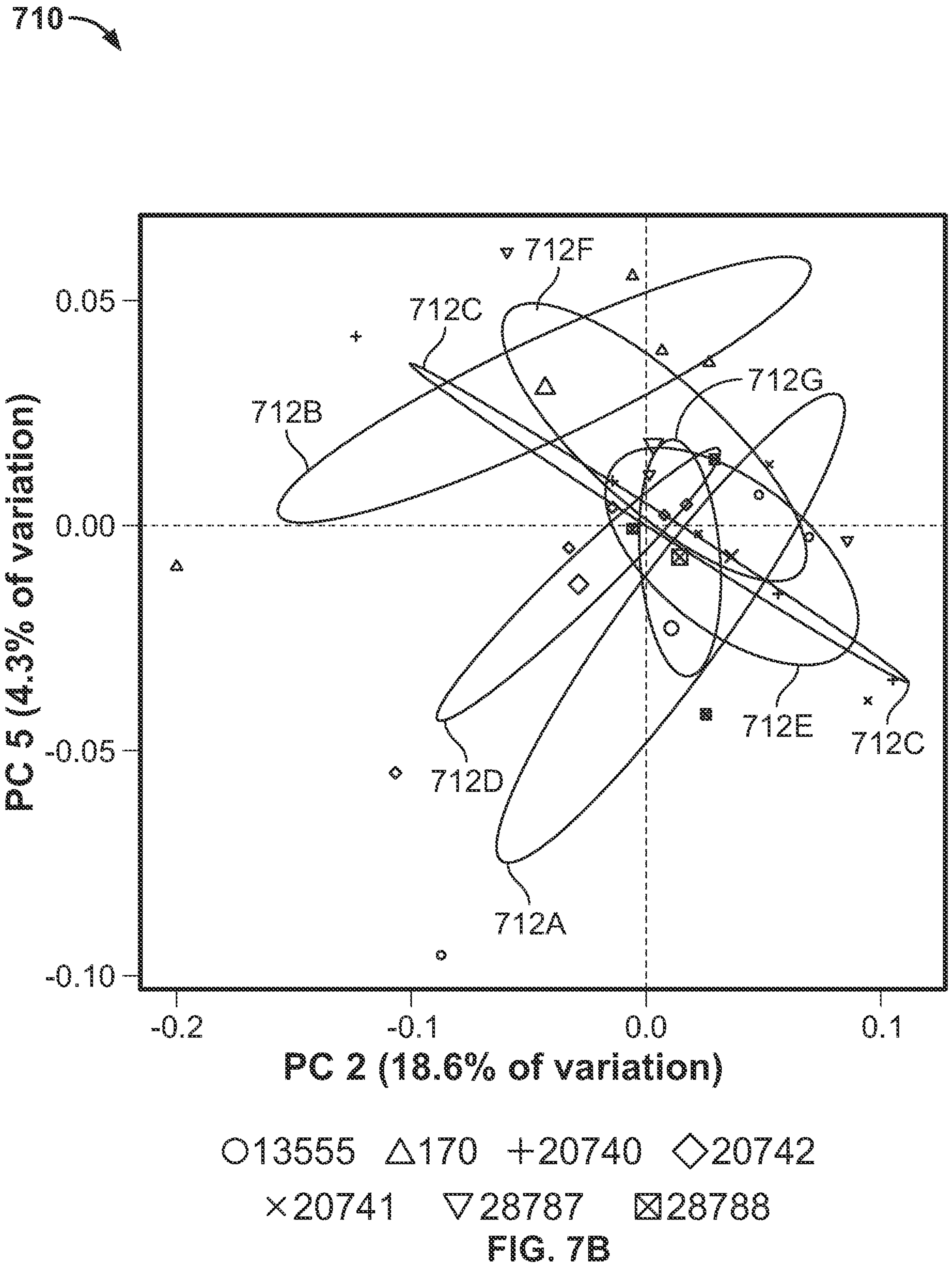
Figure 7C:
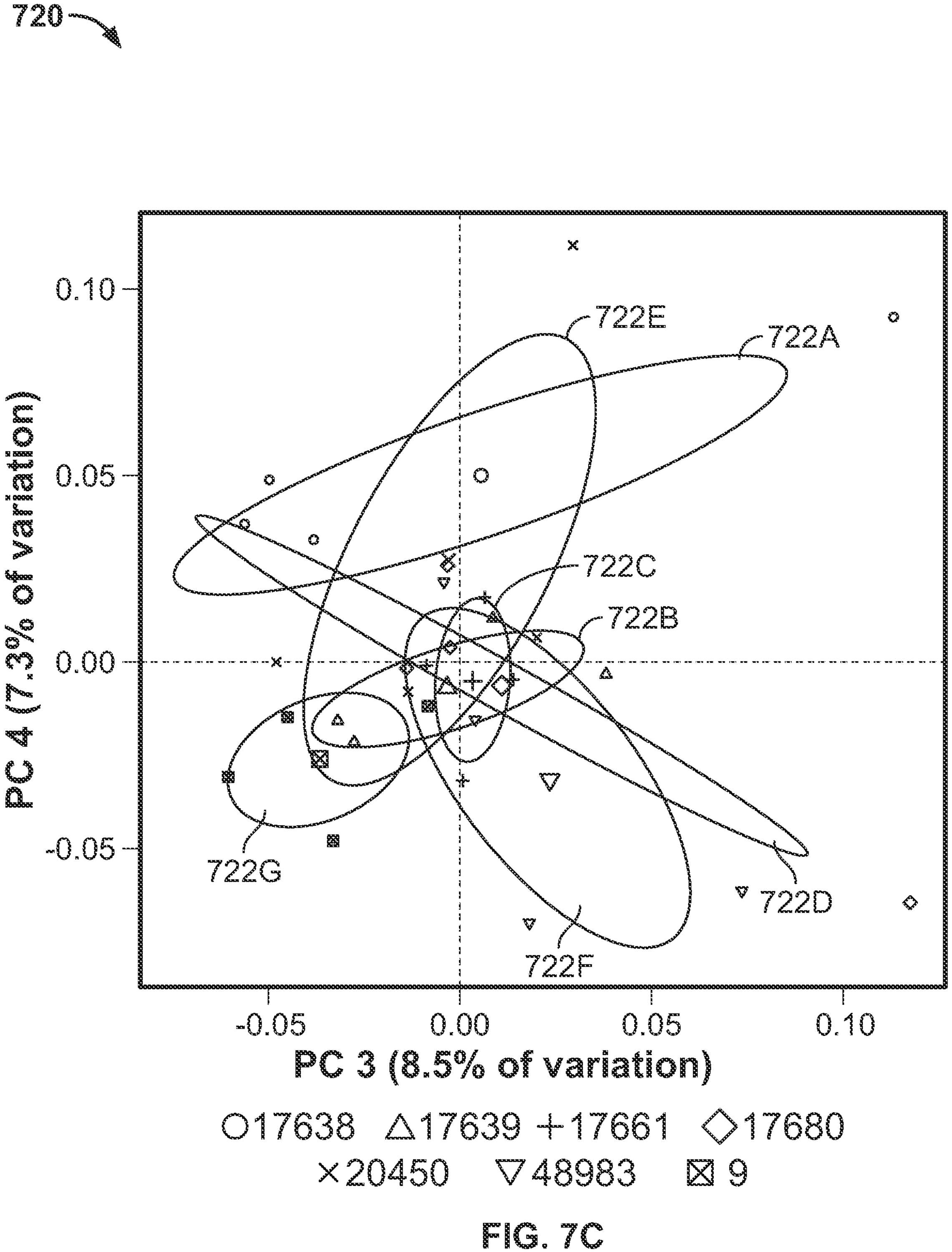

FIGS. 7A-7C are principle component analysis scatter plots 700, 710, 720 showing clusters of samples based on their similarity. Principle component analysis (PCA) is a dimensionality reduction statistical technique that creates independent "principal component" (PC) variables by combining molecular features to account for variances in a dataset. In some implementations, a PCA may be used to appraise the capability of the observed molecular features to distinguish species.

In some implementations, the mass spectral data may be imported into a commercial statistical analysis software, e.g., RStudio. In some instances, after importing the mass spectral data may be binned to m/z=0.01, and normalized to a total ion current. In some instances, background including molecular features originating from the liquid solvent and nutrient blood agar may be subtracted from the mass spectral data. In some implementations, a principle component analysis is performed on the processed mass spectral data and results including classification can be returned. For example, a prcomp function in RStudio is used. In some implementations, results may be plotted in a PCA plot to visualize grouping of samples based on the molecular features and the similarity.

As shown in FIG. 7A, different linear combinations of PC2 and PC4 (e.g., clusters) can separate different Group A *Strep.* strains. For example, a first cluster 702A corresponds to Group A *Strep.* strain 12344; a second cluster 702B corresponds to Group A *Strep.* strain 14289; a third cluster 702C corresponds to Group A *Strep.* strain 19615; a fourth cluster 702D corresponds to Group A *Strep.* strain 49399; and a fifth cluster 702E corresponds to Group A *Strep.* strain 51339. Group A *Strep.* showed the greatest degree of separation. Ninety percent confidence intervals for Group A *Strep.* strains 12344, 49399, and 14289 fully separated in the PCA scatter plot 700. The ions contributing to this separation include PG 32:0 (m/z 721.501) $[M-H]^-$, pentose phosphate (m/z 421.076) $[M-H]^-$, and acetyl-aspartic acid (m/z 174.041) $[M-H]^-$.

As shown in FIG. 7B, different linear combinations of PC2 and PC5 (e.g., clusters) can separate different *Salmonella enterica* strains. For example, a first cluster 712A corresponds to *Salmonella enterica* strain 13555; a second cluster 712B corresponds to *Salmonella enterica* strain 170; a third cluster 712C corresponds to *Salmonella enterica* strain 20740; a fourth cluster 712D corresponds to *Salmonella enterica* strain 20742; a fifth cluster 712E corresponds to *Salmonella enterica* strain 20741; a sixth cluster 712F corresponds to *Salmonella enterica* strain 28787; and a seventh cluster 712G corresponds to *Salmonella enterica* strain 28788. *Salmonella enterica* (b,e) strains 170, 20742, and 13555 can be distinguished by 90% confidence intervals. m/z features contributing to the separation for *S. enterica* strains include glutamate (m/z 174.041) $[M-H]^-$, PE 34:2 (m/z 714.504) $[M-H]^-$, and PE 34:1 (m/z 716.524) [M−H].

As shown in FIG. 7C, different linear combinations of PC3 and PC4 (e.g., clusters) can separate different *E. coli* strains. For example, a first cluster 722A corresponds to *E. coli* strain 17638; a second cluster 722B corresponds to *E.*

*coli* strain 17639; a third cluster 722C corresponds to *E. coli* strain 17661; a fourth cluster 722D corresponds *E. coli* strain 17680; a fifth cluster 722E corresponds to *E. coli* strain 20450; a sixth cluster 722F corresponds to *E. coli* strain 48983; and a seventh cluster 722G corresponds to *E. coli* strain 9. *E. coli* strains 17638, 9, and 48983 can be distinguished by 90% confidence intervals. m/z features contributing to the separation for *E. coli* strains include glutamate (m/z 174.041) $[M-H]^-$, PE 34:2 (m/z 714.504) [M−H]−, and PE 34:1 (m/z 716.524) [M−H].

Figure 7D:
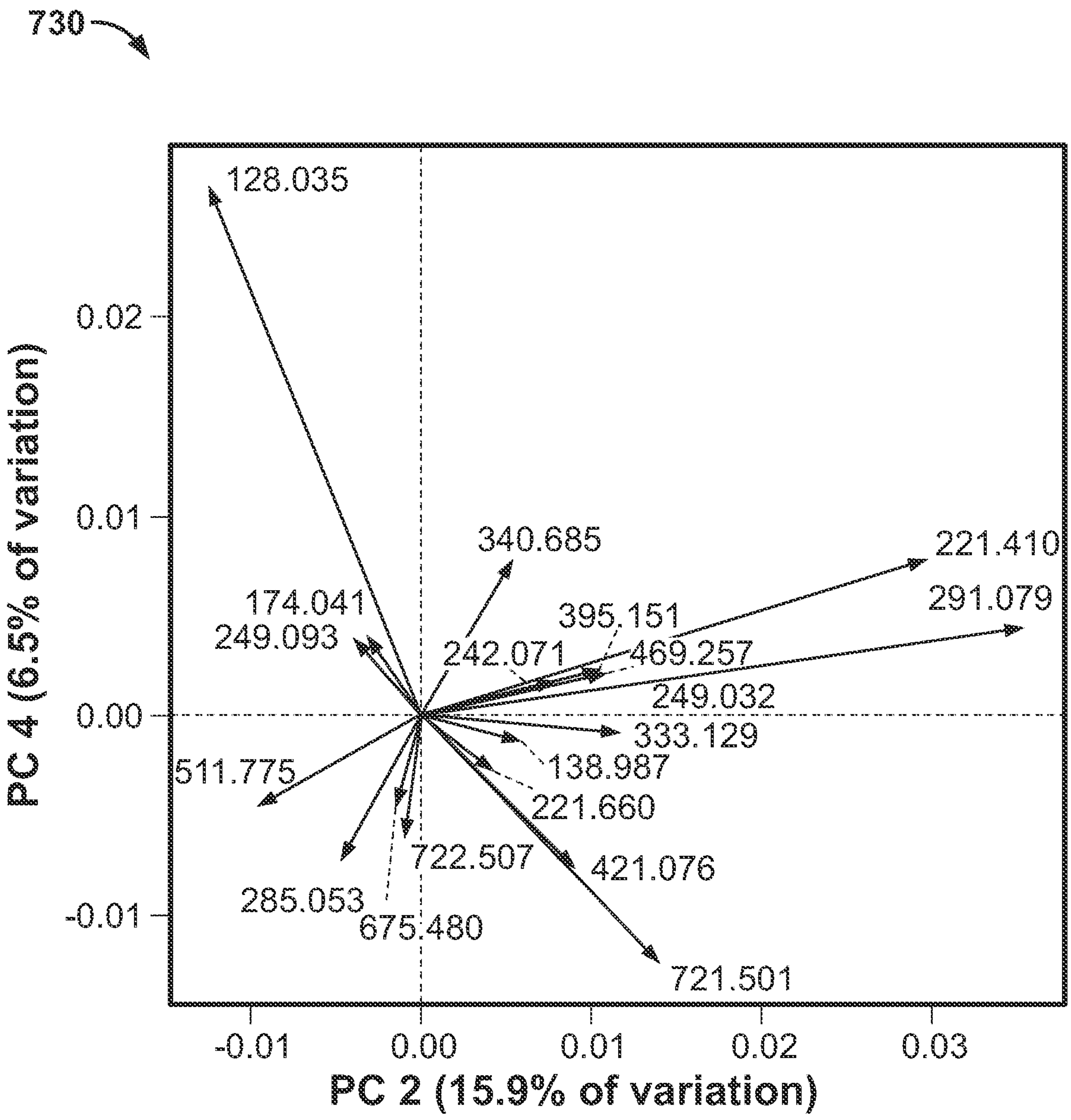
FIGS. 7D-7F are loading plots showing influence strengths of molecular features to respective principle components.
Figure 7E:
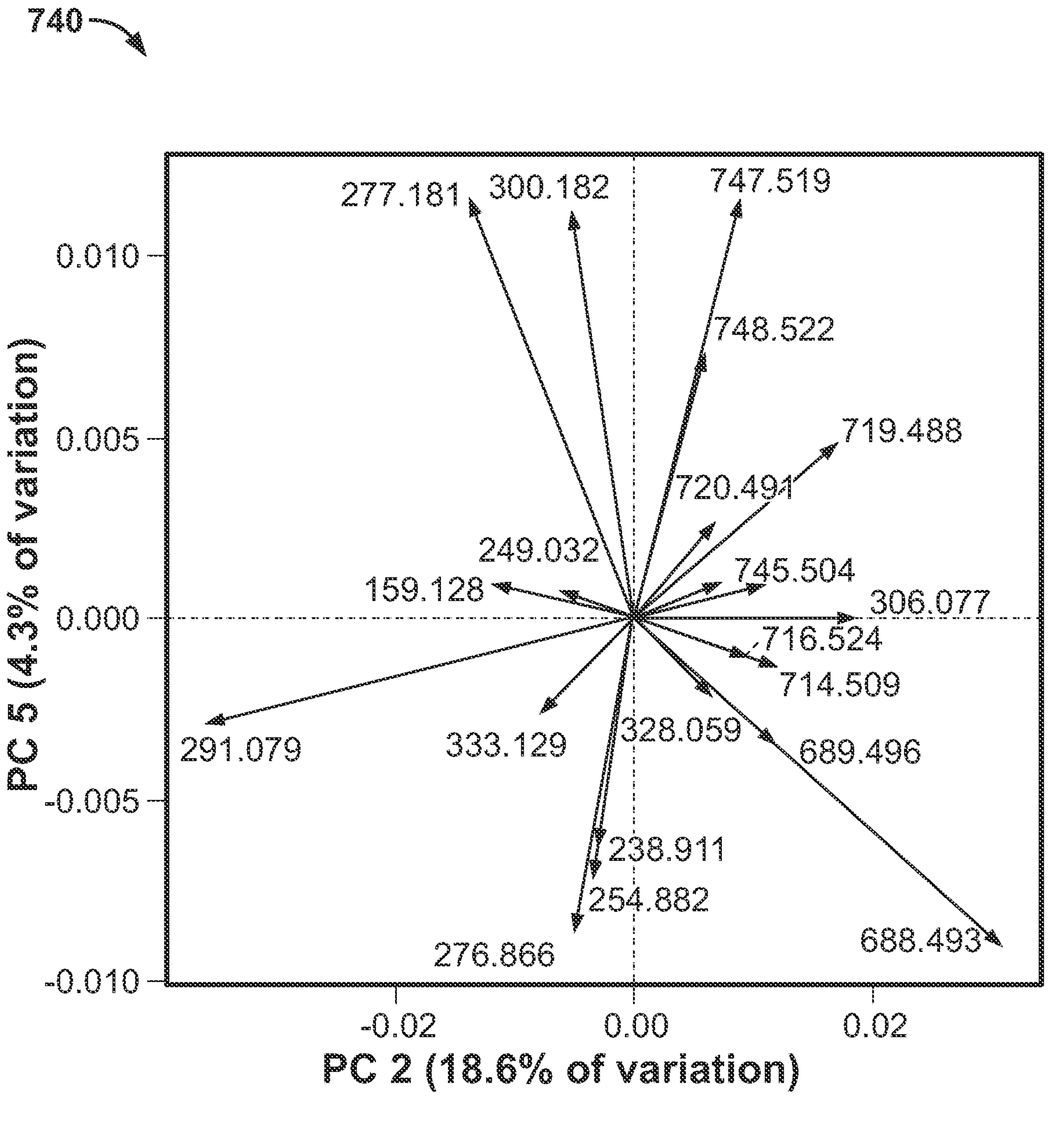
Figure 7F:
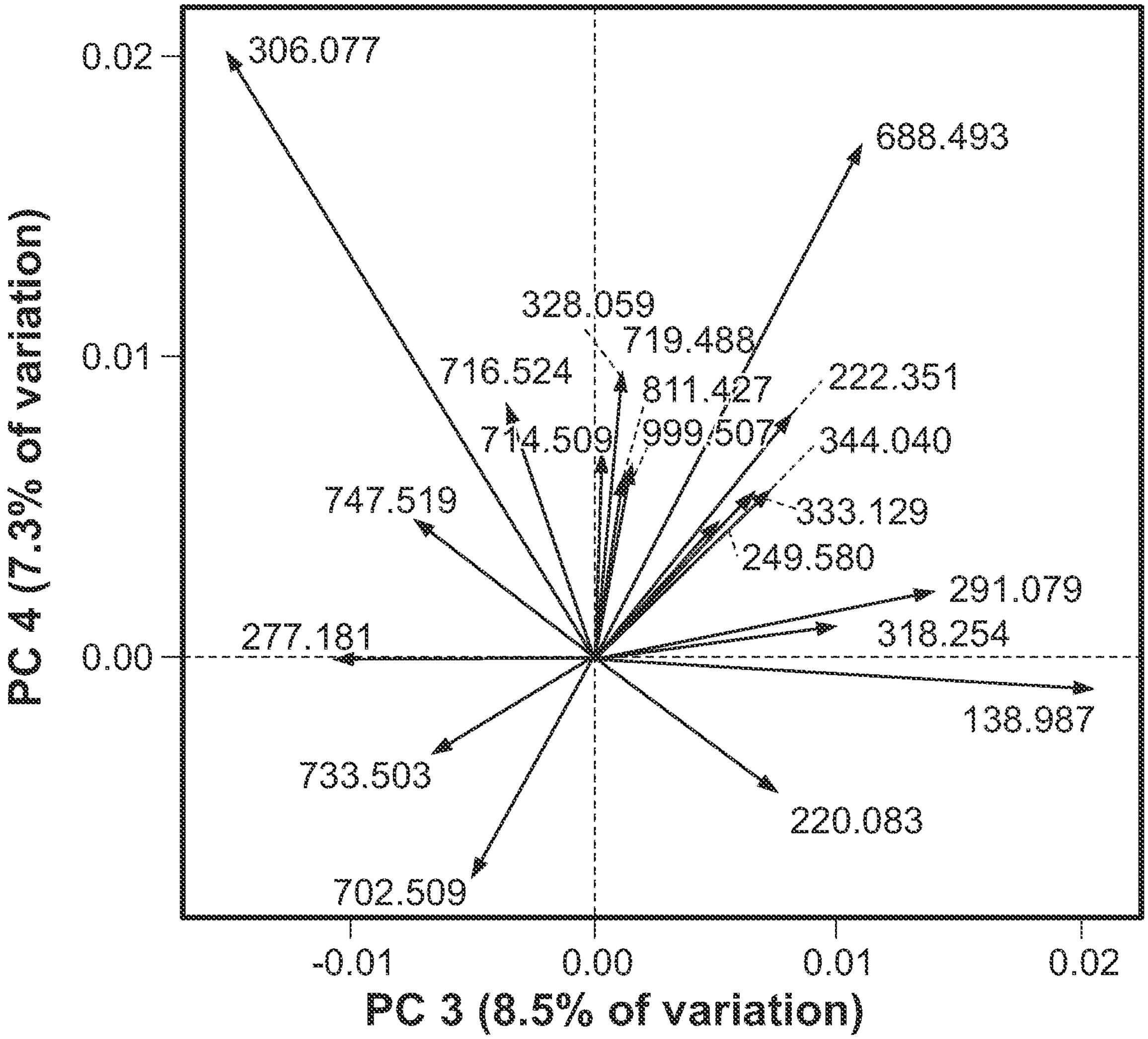

FIGS. 7D-7F are loading plots 730, 740, 750 showing influence strengths of molecular features to respective principle components. The top 20 m/z features contributing to the separation of Group A *Strep*. strains are included in FIG. 7D. The top 20 m/z features contributing to the separation of *S. enterica* strains are included in FIG. 7E. The top 20 m/z features contributing to the separation of *S. enterica* strains are included in FIG. 7E.

FIGS. 8A-8D are example tandem mass spectra and constructed molecular structures of various molecules identified in bacteria samples. In the examples shown, the tandem mass spectra from a tandem mass spectrometry analysis are used to confirm identities and to reconstruct the molecular structures of respective molecules. In some instances, the tandem mass spectra can be used to differentiate molecules with the same mass or may be used in another manner. In some instances, a single molecule is selected, fragmented into pieces, and analyzed by a mass spectrometer. The example tandem mass spectrometry analysis represented in FIGS. 8A-8D is performed using a microorganism identification system, e.g., the microorganism system as shown in FIGS. 1-2. The bacteria samples are prepared and measured as described in FIG. 4 using a sampling probe (e.g., the sampling probe 300 as shown in FIG. 3) with water as a solvent and 3-10 seconds extraction time on a QExactive HF (ThermoFisher) using collision-induced dissociation (CID).

Figure 8A:
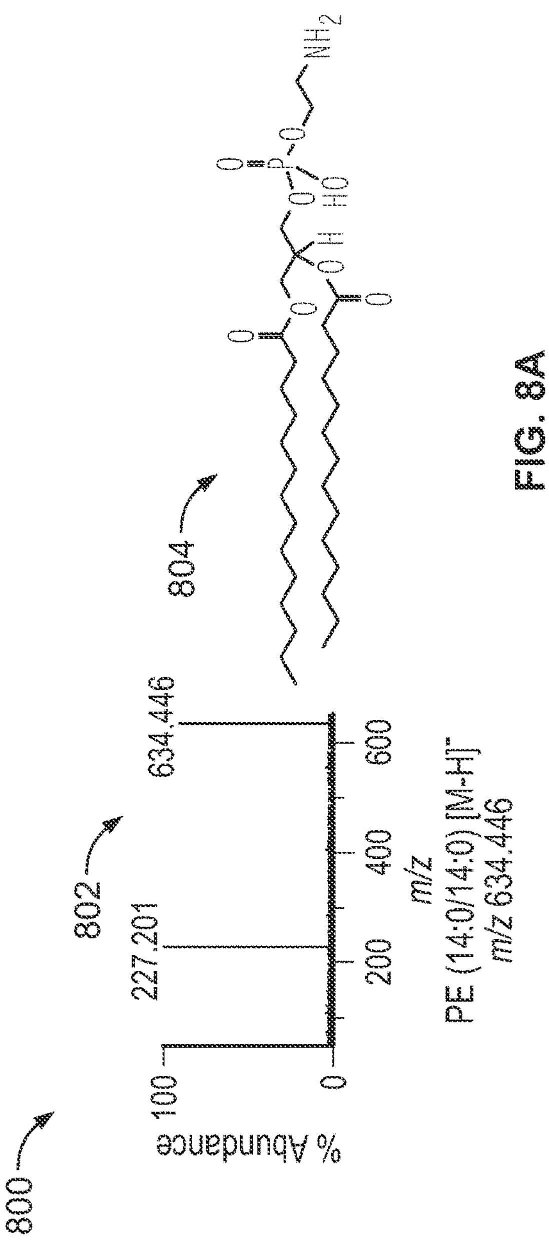
FIGS. 8A-8D are example tandem mass spectra and constructed molecular structures of various molecules identified in bacteria samples.
Figure 8B:
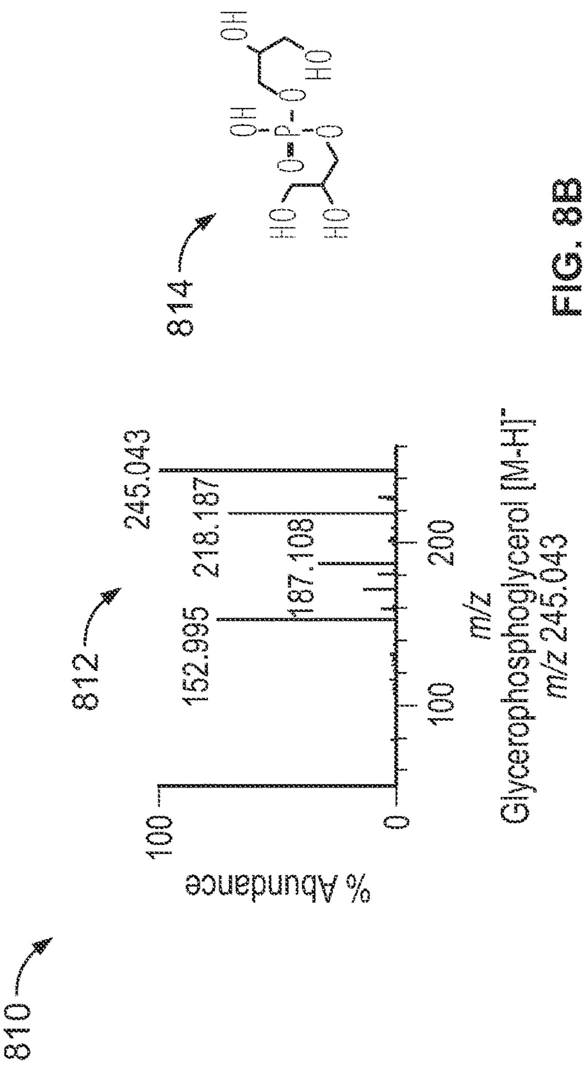
Figure 8C:
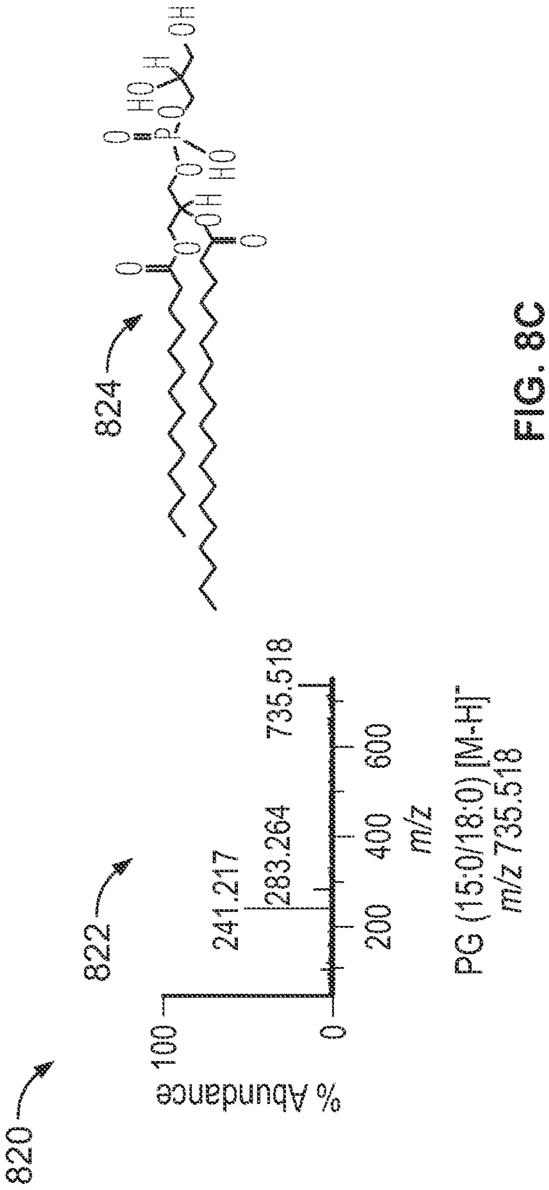
Figure 8D:
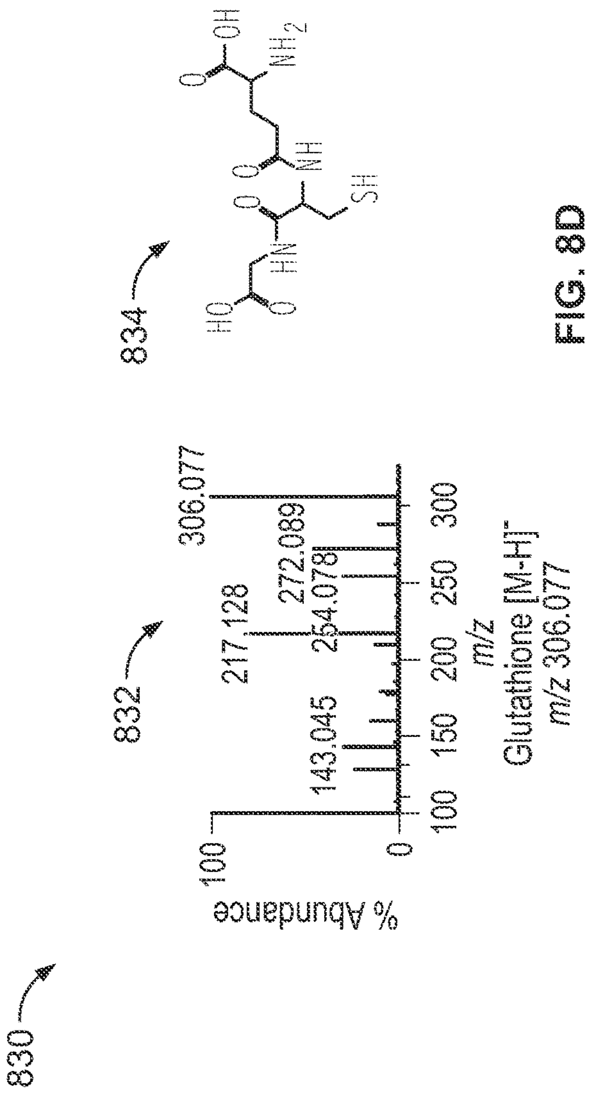

FIG. 8A shows a first tandem mass spectra 802 and a first molecular structure 804 of glycerophosphoethanolamines (PE) (14:0/14:0) with two significant peaks at m/z=634.446 and m/z=227.201. FIG. 8B shows a second tandem mass spectra 812 and a second molecular structure 814 of glycerophosphoglycerol (PG) with four significant peaks at m/z=152.995, m/z=187.108, m/z=218.187 and m/z=245.043. FIG. 8C shows a third tandem mass spectra 822 and a third molecular structure 824 of PG (15:0/18:0) with three significant peaks at m/z=241.217, m/z=283.264 and m/z=731.518. FIG. 8D shows a fourth tandem mass spectra 832 and a fourth molecular structure 834 of glutathione with five significant peaks at m/z=143.045, m/z=217.128, m/z=254.078, m/z=272.089, and m/z=306.077.

Some of the subject matter and operations described in this specification can be implemented in digital electronic circuitry, or in computer software, firmware, or hardware, including the structures disclosed in this specification and their structural equivalents, or in combinations of one or more of them. Some of the subject matter described in this specification can be implemented as one or more computer programs, i.e., one or more modules of computer program instructions, encoded on a computer storage medium for execution by, or to control the operation of, data-processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media.

Some of the operations described in this specification can be implemented as operations performed by a data processing apparatus on data stored on one or more computer-readable storage devices or received from other sources.

The term "data-processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an Arduino board, an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

In a general aspect of what is described above, microorganisms are identified and classified.

In a first example, a liquid solvent is supplied to a sample surface via a first channel of a sampling probe by operation of a control system. The liquid solvent interacts with the sample surface to form an analyte in the sampling probe. The analyte is transferred from the sampling probe via a second channel of the sampling probe. The analyte is transferred to a mass spectrometer, and the mass spectrometer processes the analyte to produce mass spectrometry data. The mass spectrometry data are analyzed to detect (e.g., to detect the presence of, or a level of) a microorganism in the analyte. The microorganism may be identified and classified, for example, using the mass spectrometry data and a statistical model.

Implementations of the first example may include one or more of the following features. The liquid solvent is supplied via the first channel to an internal reservoir of the sampling probe, and the analyte is communicated from the internal reservoir via the second channel. The sampling probe includes a gas channel that can communicate gas (e.g., air) to the internal reservoir. The internal reservoir interfaces with the sample surface, and the liquid solvent in the internal reservoir contacts the sample surface via an opening of the internal reservoir. The sample surface may include bacteria, and the mass spectrometry data may be analyzed to detect the bacteria. The analysis may include identifying and classifying the bacteria. The sample surface may include an infectious tissue specimen or another type of biological specimen. The liquid solvent may be water or another type of solvent. The liquid solvent may include bacteriolytic enzymes or other solvent additives. Intercellular biomolecules may be extracted by the bacteriolytic enzymes. The statistical model can be trained based on molecular features in mass spectral data generated by the mass spectrometer.

In a second example, a liquid solvent is supplied through a first channel of a sampling probe to an internal reservoir of the sampling probe. A fixed volume of the liquid solvent in the internal reservoir is held in direct contact with a sample surface for a period of time to form a liquid analyte in the sampling probe. Gas is supplied to the internal reservoir of the sampling probe through a second channel of the sampling probe. The liquid analyte is extracted from the internal reservoir through a third channel of the sampling probe. The liquid analyte is transferred from the sampling probe to a mass spectrometer. By operation of the mass spectrometer, the liquid analyte is processed to produce mass spectrometry data. The mass spectrometry data is analyzed to detect and identify a microorganism present at the sample surface.

Implementations of the second example may include one or more of the following features. Detecting and identifying a microorganism present at the sample surface may include detecting and identifying a microorganism on an exterior of the sample surface or within the sample surface (e.g., beneath an outermost part of the sample surface). The microorganism is classified using the mass spectrometry data and a statistical model. The first channel receives the liquid solvent from an external container through a first transfer tube, and the liquid analyte is transferred from the sampling probe to the mass spectrometer through a second transfer tube, and the second channel receives the gas through an open port that receives air from an atmosphere of the sampling probe. When the mass spectrometry data is analyzed, a bacteria present at the sample surface is identified.

Implementations of the second example may include one or more of the following features. When a bacteria present at the sample surface is identified, the presence of *Streptococcus* (*Str.*) *agalactiae* bacteria at the sample surface is identified. When a bacteria present at the sample surface is identified, the presence of *Str. pyogenes* bacteria at the sample surface is identified. When a bacteria present at the sample surface is identified, the presence of *Staphylococcus* (*S.*) *aureus* bacteria at the sample surface is identified. When a bacteria present at the sample surface is identified, the presence of *S. epidermidis* bacteria at the sample surface is identified. When a bacteria present at the sample surface is identified, the presence of *Pseudomonas* (*P.*) *aeruginosa* bacteria at the sample surface is identified. When a bacteria present at the sample surface is identified, the presence of *Salmonella enterica* bacteria at the sample surface is identified. When a bacteria present at the sample surface is identified, the presence of *Escherichia coli* bacteria at the sample surface is identified. When a bacteria present at the sample surface is identified, the presence of *Kingella* (*K.*) *kingae* bacteria at the sample surface is identified.

Implementations of the second example may include one or more of the following features. The liquid analyte is formed without producing microdroplets or aerosols in an open environment of the sample surface. The third channel of the sampling probe is coupled to the mass spectrometer by a transfer tube. When the liquid analyte from the internal reservoir is extracted, a low pressure is created in the mass spectrometer. The sampling probe is a handheld sampling probe. The sample surface includes a tissue site. The sample surface includes an infected tissue specimen. The sample surface includes an ex vivo tissue site. The sample surface includes an in vivo tissue site. The method is performed during a medical procedure. The method is performed during a surgical procedure. The tissue site is associated with a patient, and a treatment for the patient is determined based on the microorganism identified from the analysis of the mass spectrometry data. The treatment is administered to the patient.

In a third example, a system includes a container, a mass spectrometer system, a computer system, a sampling probe, and a control system. The container includes a liquid solvent. The mass spectrometer system is configured to produce mass spectrometry data by processing a liquid analyte. The computer system is configured to analyze the mass spectrometry data to detect and identify a microorganism present at a sample surface; The sampling probe includes an internal reservoir, a first channel, a second channel, a third channel. The internal reservoir is configured to hold a fixed volume of the liquid solvent in direct contact with the sample surface for a period of time to form the liquid analyte in the sampling probe. The first channel is configured to communicate the liquid solvent into the internal reservoir. The second channel configured to communicate gas into the internal reservoir; the third channel configured to communicate the liquid analyte from the internal reservoir. The control system is configured to perform operations including supplying the liquid solvent to the internal reservoir through the first channel of a sampling probe; extracting the liquid analyte from the internal reservoir through the third channel of the sampling probe; and transferring the liquid analyte from the sampling probe to the mass spectrometer system.

Implementations of the third example may include one or more of the following features. The computer system is configured to classify the microorganism using the mass spectrometry data and a statistical model. The system includes a first transfer tube that communicates the liquid solvent from the container to the first channel; and a second transfer tube that communicates the liquid analyte from the sampling probe to the mass spectrometer. The second channel includes an open end that receives air from an atmosphere of the sampling probe. The fixed volume is defined by the volume of the internal reservoir. When the mass spectrometry data is analyzed, a bacteria present at the sample surface is identified.

Implementations of the third example may include one or more of the following features. When a bacteria present at the sample surface is identified, the presence of *Streptococcus* (*Str.*) *agalactiae* bacteria at the sample surface is identified. When a bacteria present at the sample surface is identified, the presence of *Str. pyogenes* bacteria at the sample surface is identified. When a bacteria present at the sample surface is identified, the presence of *Staphylococcus* (*S.*) *aureus* bacteria at the sample surface is identified. When a bacteria present at the sample surface is identified, the presence of *S. epidermidis* bacteria at the sample surface is identified. When a bacteria present at the sample surface is identified, the presence of *Pseudomonas* (*P.*) *aeruginosa* bacteria at the sample surface is identified. When a bacteria present at the sample surface is identified, the presence of *Salmonella enterica* bacteria at the sample surface is identified. When a bacteria present at the sample surface is identified, the presence of *Escherichia coli* bacteria at the sample surface is identified. When a bacteria present at the sample surface is identified, the presence of *Kingella* (*K.*) *kingae* bacteria at the sample surface is identified.

Implementations of the third example may include one or more of the following features. The probe is configured to form the liquid analyte without producing microdroplets or aerosols in an open environment of the sample surface. The system includes a transfer tube that communicates the liquid analyte from the sampling probe to the mass spectrometer. When the liquid analyte is extracted from the internal reservoir, a low pressure is created in the mass spectrometer. The sampling probe is a handheld sampling probe. The handheld sampling probe is configured to allow use without geometrical or spatial constraints. The sample surface includes a tissue site. The sample surface includes an infected tissue specimen. The sample surface includes an ex vivo tissue site. The sample surface includes an in vivo tissue site.

While this specification contains many details, these should not be understood as limitations on the scope of what may be claimed, but rather as descriptions of features specific to particular examples. Certain features that are described in this specification or shown in the drawings in the context of separate implementations can also be combined. Conversely, various features that are described or shown in the context of a single implementation can also be implemented in multiple implementations separately or in any suitable sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single product or packaged into multiple products.

A number of embodiments have been described. Nevertheless, it will be understood that various modifications can be made. Accordingly, other embodiments are within the scope of the present disclosure.

What is claimed is:

1. A method comprising:

supplying a liquid solvent through a first channel of a sampling probe to an internal reservoir of the sampling probe, the internal reservoir having an opening at a tip of the sampling probe;

holding a fixed volume of the liquid solvent in the internal reservoir in direct contact with a sample surface for a period of time to form a liquid analyte in the sampling probe, wherein the tip of the sampling probe is in direct contact with the sample surface such that the liquid solvent is in direct contact with the sample surface via the opening at the tip of the sampling probe, and therefore the liquid analyte is formed without producing microdroplets or aerosols in an open environment of the sample surface;

supplying gas to the internal reservoir of the sampling probe through a second channel of the sampling probe, wherein the second channel receives the gas through an open port that receives air from an atmosphere of the sampling probe;

extracting the liquid analyte from the internal reservoir through a third channel of the sampling probe;

transferring the liquid analyte from the sampling probe to a mass spectrometer;

by operation of the mass spectrometer, processing the liquid analyte to produce mass spectrometry data; and analyzing the mass spectrometry data to detect and identify a microorganism present at the sample surface.

2. The method of claim 1, comprising classifying the microorganism using the mass spectrometry data and a statistical model.

3. The method of claim 1, wherein the first channel receives the liquid solvent from an external container through a first transfer tube, and the liquid analyte is transferred from the sampling probe to the mass spectrometer through a second transfer tube.

4. The method of claim 1, wherein analyzing the mass spectrometry data comprises identifying a bacteria present at the sample surface.

5. The method of claim 1, wherein identifying a bacteria present at the sample surface comprises identifying the presence of *Streptococcus* (*Str.*) *agalactiae* bacteria, *Str. pyogenes* bacteria, *Staphylococcus* (*S.*) *aureus* bacteria, *S. epidermidis* bacteria, *Pseudomonas* (*P.*) *aeruginosa* bacteria, *Salmonella enterica* bacteria, *Escherichia coli* bacteria, *Kingella* (*K.*) *kingae* bacteria, or a combination thereof at the sample surface.

6. The method of claim 1, wherein the third channel of the sampling probe is coupled to the mass spectrometer by a transfer tube, and extracting the liquid analyte from the internal reservoir comprises creating a low pressure in the mass spectrometer.

7. The method of claim 1, wherein the sampling probe is a handheld sampling probe.

8. The method of claim 1, wherein the sample surface comprises a tissue site.

9. The method of claim 8, wherein the tissue site comprises an infected tissue specimen.

10. The method of claim 8, wherein the sample surface comprises an ex vivo tissue site or an in vivo tissue site.

11. The method of claim 1, performed during a medical or surgical procedure.

12. The method of claim 8, wherein the tissue site is associated with a patient, and the method comprises determining a treatment for the patient based on the microorganism identified from the analysis of the mass spectrometry data.

13. The method of claim 12, further comprising administering the treatment to the patient.

* * * * *